(12) United States Patent
Zeiner et al.

(10) Patent No.: US 11,452,523 B2
(45) Date of Patent: Sep. 27, 2022

(54) APPARATUS AND METHOD TO APPLY BUTTRESSES SEPARATELY TO JAWS OF END EFFECTOR OF SURGICAL STAPLER

(71) Applicant: Ethicon LLC, Guaynabo, PR (US)

(72) Inventors: Mark S. Zeiner, Mason, OH (US); Heather Strang, West Chester, OH (US); Pamela M. Ridgley, Lebanon, OH (US); Christopher A. Denzinger, Cincinnati, OH (US); Christopher Q. Seow, Cincinnati, OH (US); Michael J. Vendely, Lebanon, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 126 days.

(21) Appl. No.: 17/022,214

(22) Filed: Sep. 16, 2020

(65) Prior Publication Data

US 2022/0079581 A1  Mar. 17, 2022

(51) Int. Cl.
*A61B 17/072* (2006.01)
*A61B 17/068* (2006.01)
*A61B 90/00* (2016.01)
*A61B 17/115* (2006.01)
*A61B 90/90* (2016.01)
(Continued)

(52) U.S. Cl.
CPC ........ *A61B 17/0686* (2013.01); *A61B 17/068* (2013.01); *A61B 17/072* (2013.01);
(Continued)

(58) Field of Classification Search
CPC .............. A61B 17/068; A61B 17/0682; A61B 17/0686; A61B 17/072; A61B 17/07207;
(Continued)

(56) References Cited

U.S. PATENT DOCUMENTS

| 4,930,674 A | 6/1990 | Barak |
| 5,358,510 A | 10/1994 | Luscombe et al. |

(Continued)

FOREIGN PATENT DOCUMENTS

| EP | 2 090 248 A2 | 8/2009 |
| EP | 3 072 460 A2 | 9/2016 |

(Continued)

OTHER PUBLICATIONS

Gore Seamguard Bioabsorbable Staple Line Reinforcement, Configured for Endoscopic Surgical Staplers, Instructions for Use, Jun. 2019, 136 pgs.

(Continued)

*Primary Examiner* — Scott A Smith
(74) *Attorney, Agent, or Firm* — Frost Brown Todd LLC

(57) ABSTRACT

An apparatus is configured to apply an adjunct material to a stapling surface of a jaw of a surgical stapler. The jaw includes an outer surface disposed opposite the stapling surface. The apparatus includes a housing and an arm. The housing includes a first contact feature that is configured to contact one of the adjunct material or the outer surface of the jaw. The arm is operatively coupled with the housing. The arm includes a second contact feature that is configured to move relative to the first contact feature to contact the other of the adjunct material or the outer surface of the jaw. The first and second contact features are configured to cooperate to apply a compression force in a direction toward the first contact feature to pinch the adjunct material against the stapling surface to mount the adjunct material to the stapling surface.

20 Claims, 26 Drawing Sheets

(51) Int. Cl.
*A61B 17/00* (2006.01)
*A61B 50/30* (2016.01)

(52) U.S. Cl.
CPC .. *A61B 17/07207* (2013.01); *A61B 17/07292* (2013.01); *A61B 90/03* (2016.02); *A61B 17/00491* (2013.01); *A61B 17/0682* (2013.01); *A61B 17/115* (2013.01); *A61B 50/30* (2016.02); *A61B 90/90* (2016.02); *A61B 2017/07214* (2013.01); *A61B 2017/07228* (2013.01); *A61B 2017/07264* (2013.01); *A61B 2090/037* (2016.02)

(58) Field of Classification Search
CPC ............ A61B 17/07292; A61B 17/115; A61B 17/1155; A61B 17/00491; A61B 2017/07214; A61B 2017/07228; A61B 2017/07264; A61B 50/30; A61B 50/31; A61B 90/90; A61B 90/91
USPC .............. 227/19, 175.1, 175.2, 176.1, 180.1; 606/1, 139, 219
See application file for complete search history.

(56) References Cited

U.S. PATENT DOCUMENTS

| | | |
|---|---|---|
| 5,372,868 A | 12/1994 | Prewo et al. |
| 5,655,698 A | 8/1997 | Yoon |
| 5,697,542 A | 12/1997 | Knodel et al. |
| 5,752,965 A | 5/1998 | Francis et al. |
| 5,769,892 A | 6/1998 | Kingwell |
| 5,810,855 A | 9/1998 | Rayburn et al. |
| 5,833,695 A | 11/1998 | Yoon |
| 5,901,895 A | 5/1999 | Heaton et al. |
| 5,902,312 A | 5/1999 | Frater et al. |
| 6,019,791 A | 2/2000 | Wood |
| 6,099,551 A | 8/2000 | Gabbay |
| 6,273,897 B1 | 8/2001 | Dalessandro et al. |
| 6,325,810 B1 | 12/2001 | Hamilton et al. |
| 6,592,597 B2 | 7/2003 | Grant et al. |
| 6,638,285 B2 | 10/2003 | Gabbay |
| 7,147,138 B2 | 12/2006 | Shelton, IV |
| 7,377,928 B2 | 5/2008 | Zubik et al. |
| 7,380,696 B2 | 6/2008 | Shelton, IV et al. |
| 7,559,937 B2 | 7/2009 | De La Torre et al. |
| 7,665,646 B2 | 2/2010 | Prommersberger |
| 7,708,180 B2 | 5/2010 | Murray et al. |
| 7,845,533 B2 | 12/2010 | Marczyk et al. |
| 8,052,697 B2 | 11/2011 | Phillips |
| 8,210,411 B2 | 7/2012 | Yates et al. |
| 8,317,790 B2 | 11/2012 | Bell et al. |
| 8,348,130 B2 | 1/2013 | Shah et al. |
| 8,408,439 B2 | 4/2013 | Huang et al. |
| 8,453,914 B2 | 6/2013 | Laurent et al. |
| 8,464,925 B2 | 6/2013 | Hull et al. |
| 8,864,009 B2 | 10/2014 | Shelton, IV et al. |
| 9,186,142 B2 | 11/2015 | Fanelli et al. |
| 9,211,120 B2 * | 12/2015 | Scheib ............. A61B 17/07207 |
| 9,220,501 B2 | 12/2015 | Baxter, III et al. |
| 9,517,065 B2 | 12/2016 | Simms et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,833,238 B2 | 12/2017 | Baxter, III et al. |
| 9,839,421 B2 | 12/2017 | Zerkle et al. |
| 9,999,408 B2 | 6/2018 | Boudreaux et al. |
| 10,092,292 B2 | 10/2018 | Boudreaux et al. |
| 10,166,023 B2 | 1/2019 | Vendely et al. |
| 10,213,198 B2 | 2/2019 | Aronhalt et al. |
| 10,349,939 B2 | 7/2019 | Shelton, IV et al. |
| 10,932,779 B2 | 3/2021 | Vendely et al. |
| 10,993,716 B2 | 5/2021 | Shelton, IV et al. |
| 11,033,269 B2 | 6/2021 | Vendely et al. |
| 11,045,196 B2 | 6/2021 | Olson et al. |
| 11,051,812 B2 | 7/2021 | Hopkins et al. |
| 11,058,418 B2 | 7/2021 | Shelton, IV et al. |
| 11,065,000 B2 | 7/2021 | Shankarsetty et al. |
| 2005/0267325 A1 | 12/2005 | Bouchier et al. |
| 2006/0173470 A1 | 8/2006 | Oray et al. |
| 2007/0034669 A1* | 2/2007 | de la Torre ...... A61B 17/07207 227/180.1 |
| 2007/0162056 A1 | 7/2007 | Gerbi et al. |
| 2007/0179528 A1 | 8/2007 | Soltz et al. |
| 2007/0246505 A1 | 10/2007 | Pace-Floridia et al. |
| 2008/0128469 A1 | 6/2008 | Dalessandro et al. |
| 2008/0169329 A1 | 7/2008 | Shelton et al. |
| 2008/0203134 A1 | 8/2008 | Shah et al. |
| 2009/0001122 A1 | 1/2009 | Prommersberger et al. |
| 2009/0084825 A1 | 4/2009 | Larson |
| 2009/0206125 A1* | 8/2009 | Huitema .......... A61B 17/07292 227/175.1 |
| 2009/0206126 A1 | 8/2009 | Huitema et al. |
| 2010/0087840 A1 | 4/2010 | Ebersole et al. |
| 2010/0163598 A1 | 7/2010 | Belzer |
| 2011/0017802 A1 | 1/2011 | Ma et al. |
| 2011/0087279 A1 | 4/2011 | Shah et al. |
| 2011/0248064 A1 | 10/2011 | Marczyk |
| 2012/0018487 A1 | 1/2012 | Bettuchi et al. |
| 2012/0080336 A1 | 4/2012 | Shelton, IV et al. |
| 2012/0241503 A1* | 9/2012 | Baxter, III ....... A61B 17/00491 227/176.1 |
| 2012/0265154 A1 | 10/2012 | Criscuolo et al. |
| 2013/0037596 A1 | 2/2013 | Bear et al. |
| 2013/0075447 A1 | 3/2013 | Weisenburgh, II |
| 2013/0146642 A1 | 6/2013 | Shelton, IV et al. |
| 2013/0214030 A1* | 8/2013 | Aronhalt ........... A61B 17/0686 227/176.1 |
| 2013/0256378 A1 | 10/2013 | Schmid et al. |
| 2014/0058194 A1 | 2/2014 | Soletti et al. |
| 2014/0131418 A1 | 5/2014 | Kostrzewski |
| 2014/0131419 A1 | 5/2014 | Bettuchi |
| 2014/0158741 A1 | 6/2014 | Woodard, Jr. et al. |
| 2014/0239036 A1 | 8/2014 | Zerkle et al. |
| 2014/0288386 A1 | 9/2014 | Zand et al. |
| 2014/0291379 A1 | 10/2014 | Schellin et al. |
| 2015/0041168 A1 | 2/2015 | Dostinov |
| 2015/0076212 A1 | 3/2015 | Shelton, IV |
| 2015/0351761 A1 | 12/2015 | Shelton, IV et al. |
| 2016/0278774 A1* | 9/2016 | Shelton, IV ......... A61B 17/068 |
| 2017/0055980 A1 | 3/2017 | Vendely et al. |
| 2017/0055981 A1* | 3/2017 | Vendely ............. A61B 17/068 |
| 2017/0056016 A1 | 3/2017 | Barton et al. |
| 2017/0056018 A1 | 3/2017 | Zeiner et al. |
| 2017/0281181 A1 | 10/2017 | Matonick et al. |
| 2017/0303952 A1 | 10/2017 | Nativ et al. |
| 2018/0235617 A1 | 8/2018 | Shelton, IV et al. |
| 2018/0235626 A1 | 8/2018 | Shelton, IV et al. |
| 2019/0290267 A1* | 9/2019 | Baxter, III ............ A61L 17/005 |
| 2019/0321044 A1 | 10/2019 | Franklin, Sr. |
| 2019/0343520 A1 | 11/2019 | Williams et al. |
| 2020/0015817 A1 | 1/2020 | Harris et al. |
| 2020/0205823 A1 | 7/2020 | Vendely et al. |
| 2020/0205825 A1 | 7/2020 | Vendely et al. |
| 2020/0261080 A1 | 8/2020 | Bakos et al. |
| 2020/0281587 A1* | 9/2020 | Schmid ............. A61B 17/1155 |
| 2020/0405436 A1 | 12/2020 | Shelton, IV et al. |
| 2021/0106329 A1 | 4/2021 | Williams et al. |
| 2021/0177411 A1 | 6/2021 | Williams |

FOREIGN PATENT DOCUMENTS

EP 3 632 342 A2 4/2020
EP 3 673 831 A2 7/2020

OTHER PUBLICATIONS

International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.

(56) References Cited

OTHER PUBLICATIONS

International Search Report and Written Opinion dated Dec. 2, 2021 for Application No. PCT/IB2021/058414, 14 pgs.
International Search Report and Written Opinion dated Feb. 16, 2022 for Application No. PCT/IB2021/060163, 15 pgs.
International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.
U.S. Appl. No. 17/022,186.
U.S. Appl. No. 17/022,209.
U.S. Appl. No. 17/022,414.
U.S. Appl. No. 17/022,419.
U.S. Appl. No. 17/022,442.
U.S. Appl. No. 17/022,520.
U.S. Appl. No. 17/022,186, entitled "Apparatus and Method to Apply Buttress to End Effector of Surgical Stapler via Fixed Base," filed Sep. 16, 2020.
U.S. Appl. No. 17/022,209, entitled "Apparatus and Method to Apply Buttress to End Effector of Surgical Stapler via Driven Member," filed Sep. 16, 2020.
U.S. Appl. No. 17/022,414, entitled "Apparatus and Method to Close End Effector of Surgical Stapler onto Buttress," filed Sep. 16, 2020.
U.S. Appl. No. 17/022,419, entitled "Apparatus and Method to Detect Full Seating of Buttress Applicator in End Effector of Surgical Stapler," filed Sep. 16, 2020.
U.S. Appl. No. 17/022,442, entitled "Apparatus and Method to Apply Buttress to End Effector of Surgical Stapler with Authentication," filed Sep. 16, 2020.
U.S. Appl. No. 17/022,520, entitled "Method of Applying Buttress to End Effector of Surgical Stapler," filed Sep. 16, 2020.

* cited by examiner

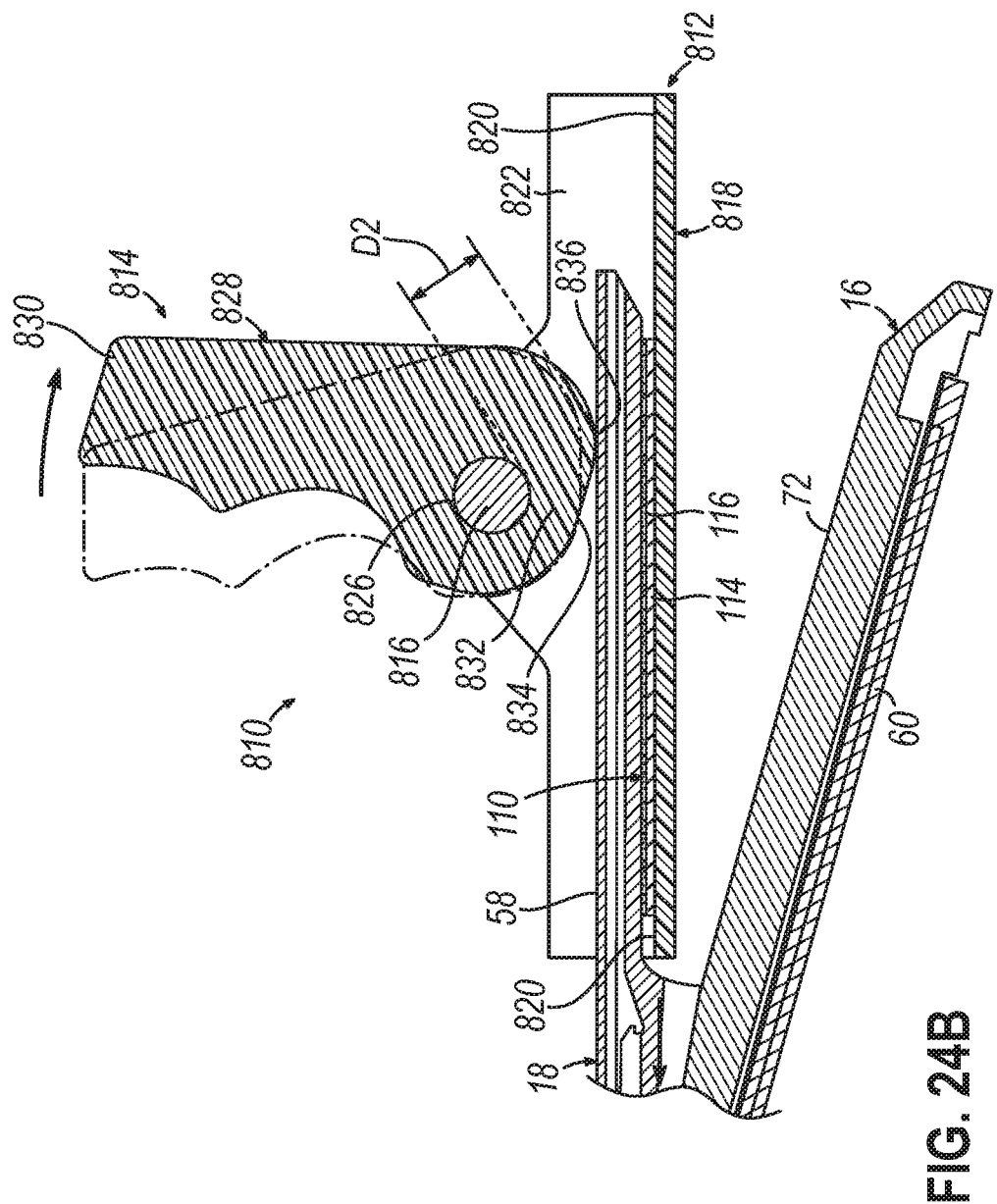

APPARATUS AND METHOD TO APPLY BUTTRESSES SEPARATELY TO JAWS OF END EFFECTOR OF SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 24B depicts a cross-sectional view of the applicator device, the buttress assembly, and the end effector of FIG. 24A, with an arm of the applicator device being rotated to apply and secure the buttress assembly to the upper jaw.

Figure 1:
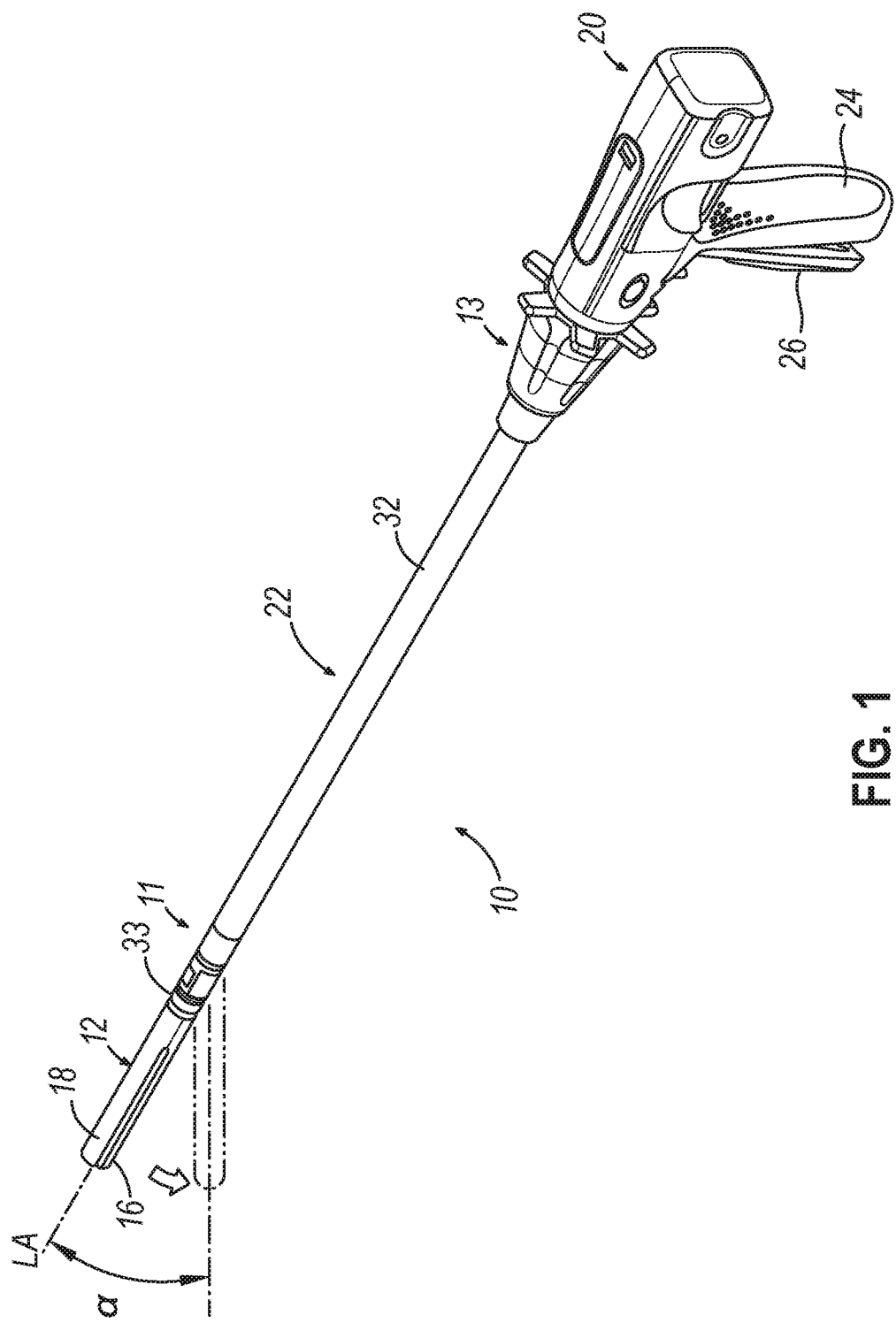
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
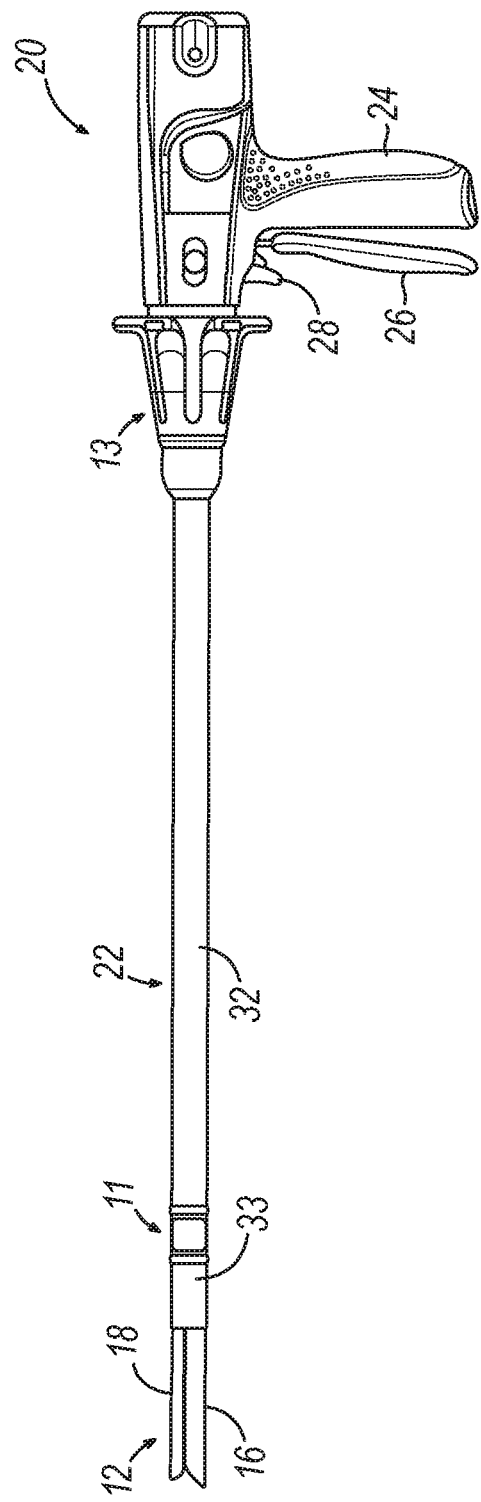
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
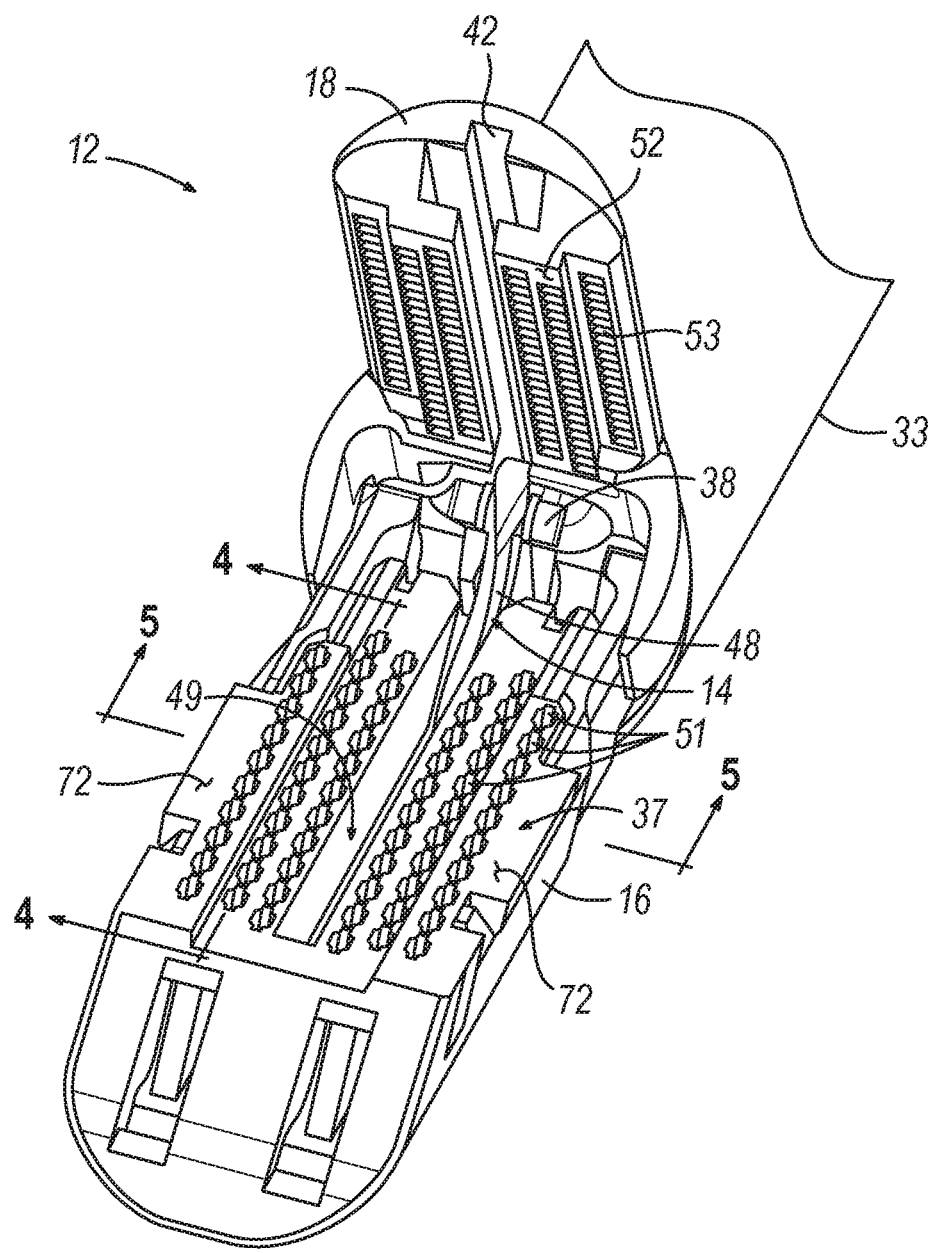
FIG. 3 depicts a perspective view of an end effector of the instrument of FIG. 1 in an open state.
Figure 4A:
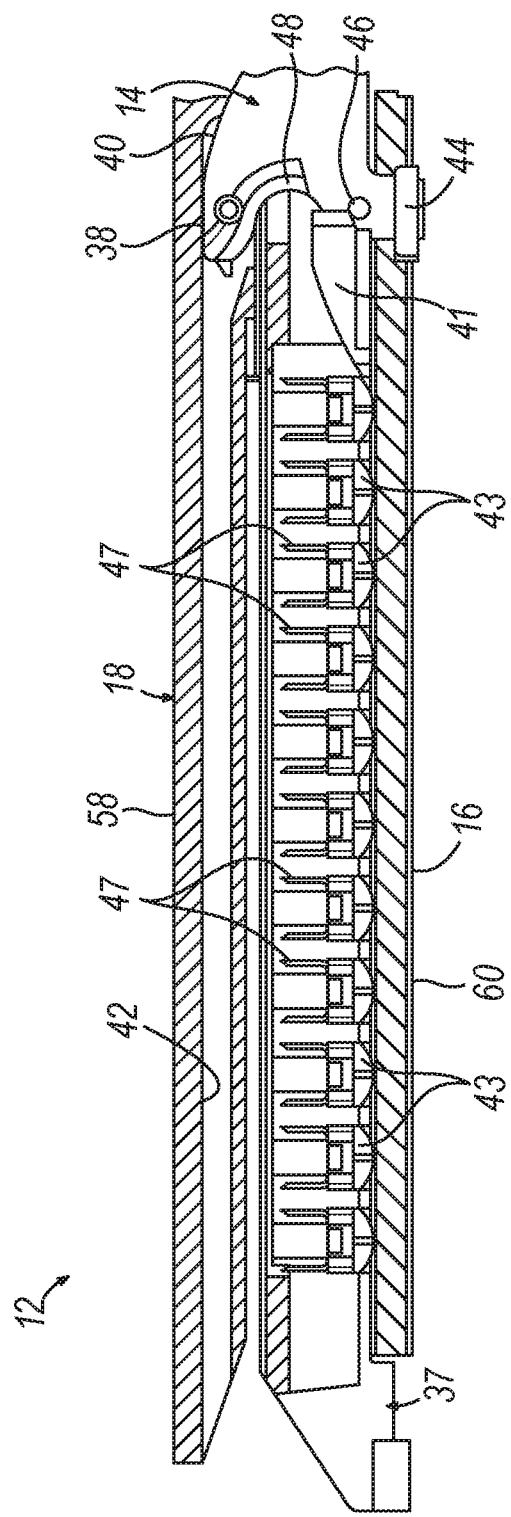
FIG. 4A depicts a side cross-sectional view of the end effector of FIG. 3, taken along line 4-4 of FIG. 3, with a firing beam in a proximal position.
Figure 4B:
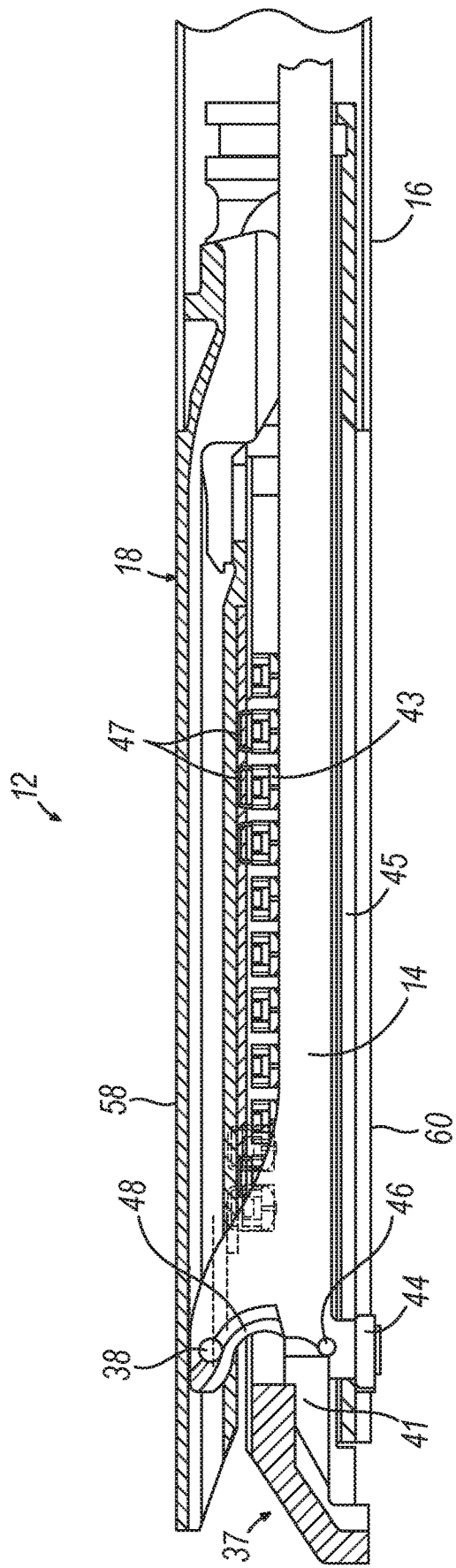
FIG. 4B depicts a side cross-sectional view of the end effector of FIG. 3, taken along line 4-4 of FIG. 3, with the firing beam in a distal position.
Figure 5:
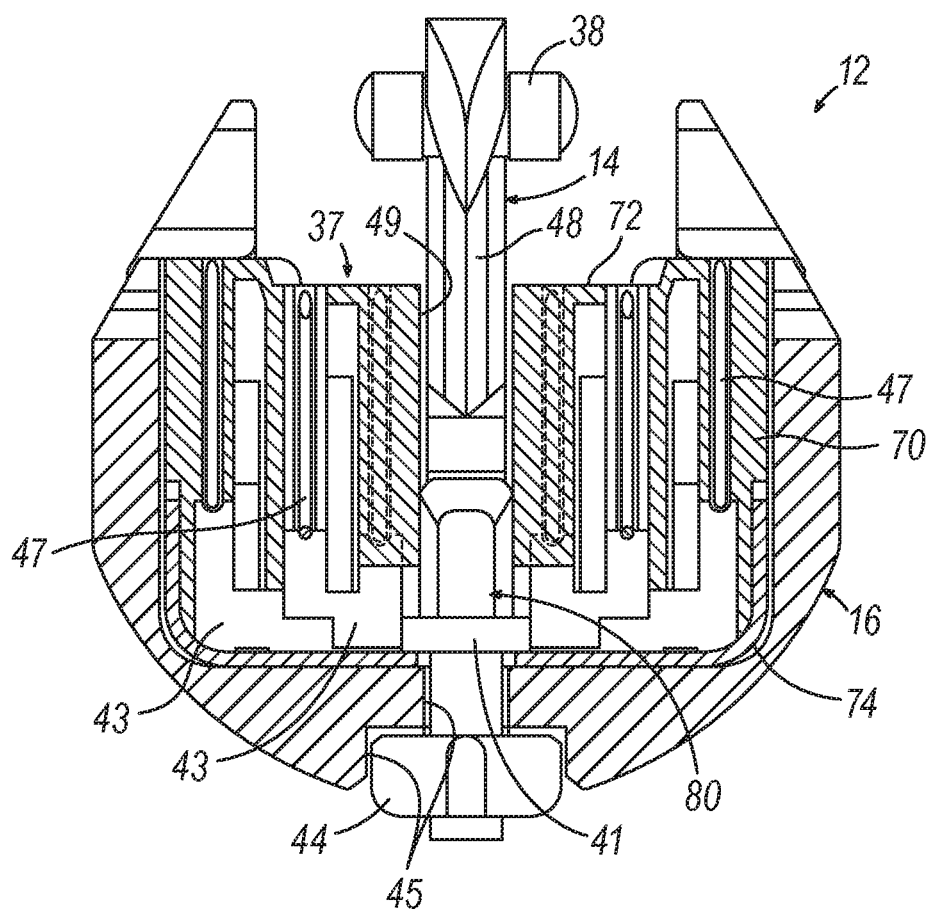
FIG. 5 depicts an end cross-sectional view of the end effector of FIG. 3, taken along line 5-5 of FIG. 3.
Figure 6:
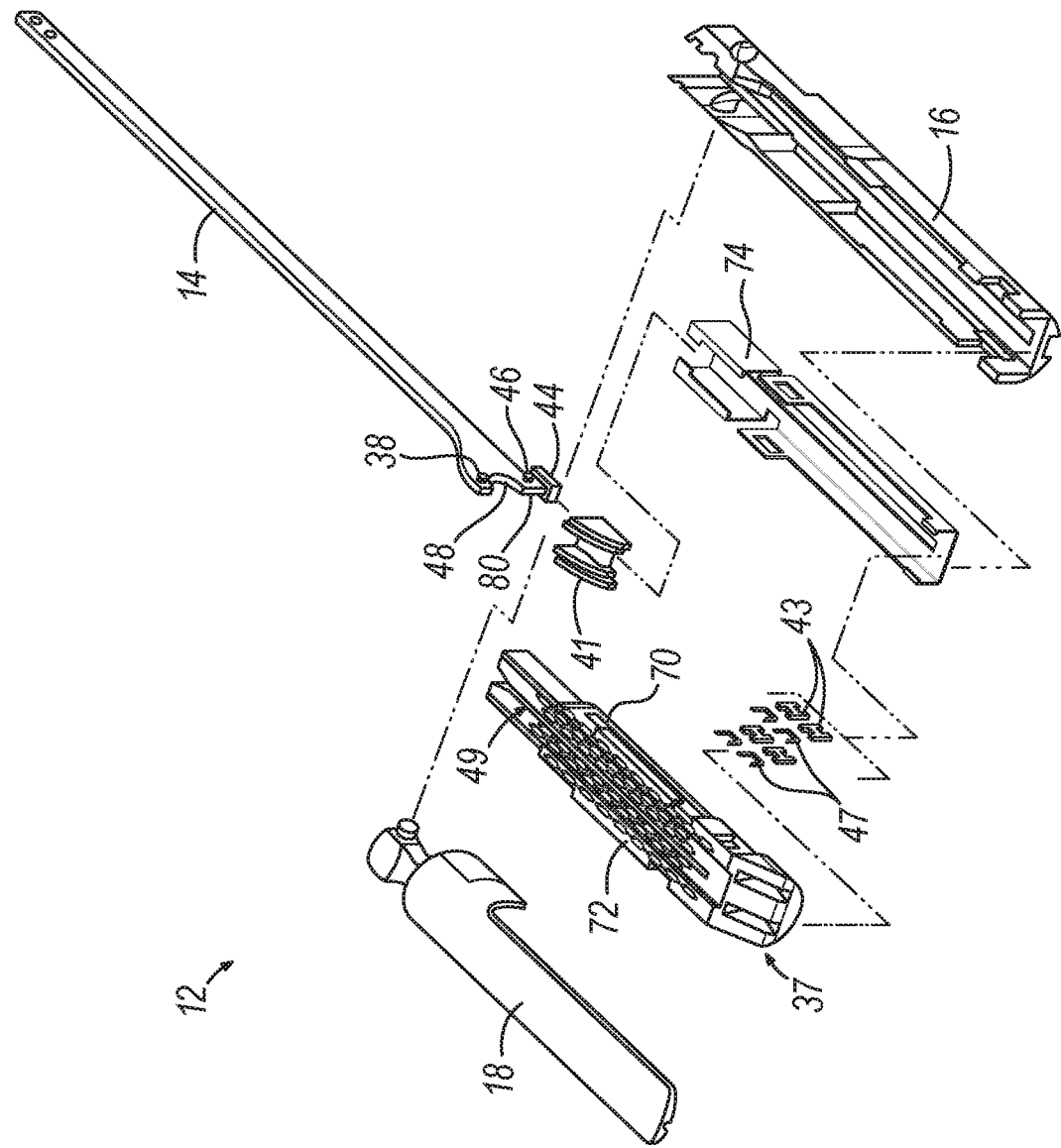
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). Upper deck (72) is disposed opposite an outer surface (60). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at the distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on a contact surface (52) of anvil (18). Anvil (18) includes proximal and distal portions (54, 56) and an outer surface (58) disposed opposite contact surface (52). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
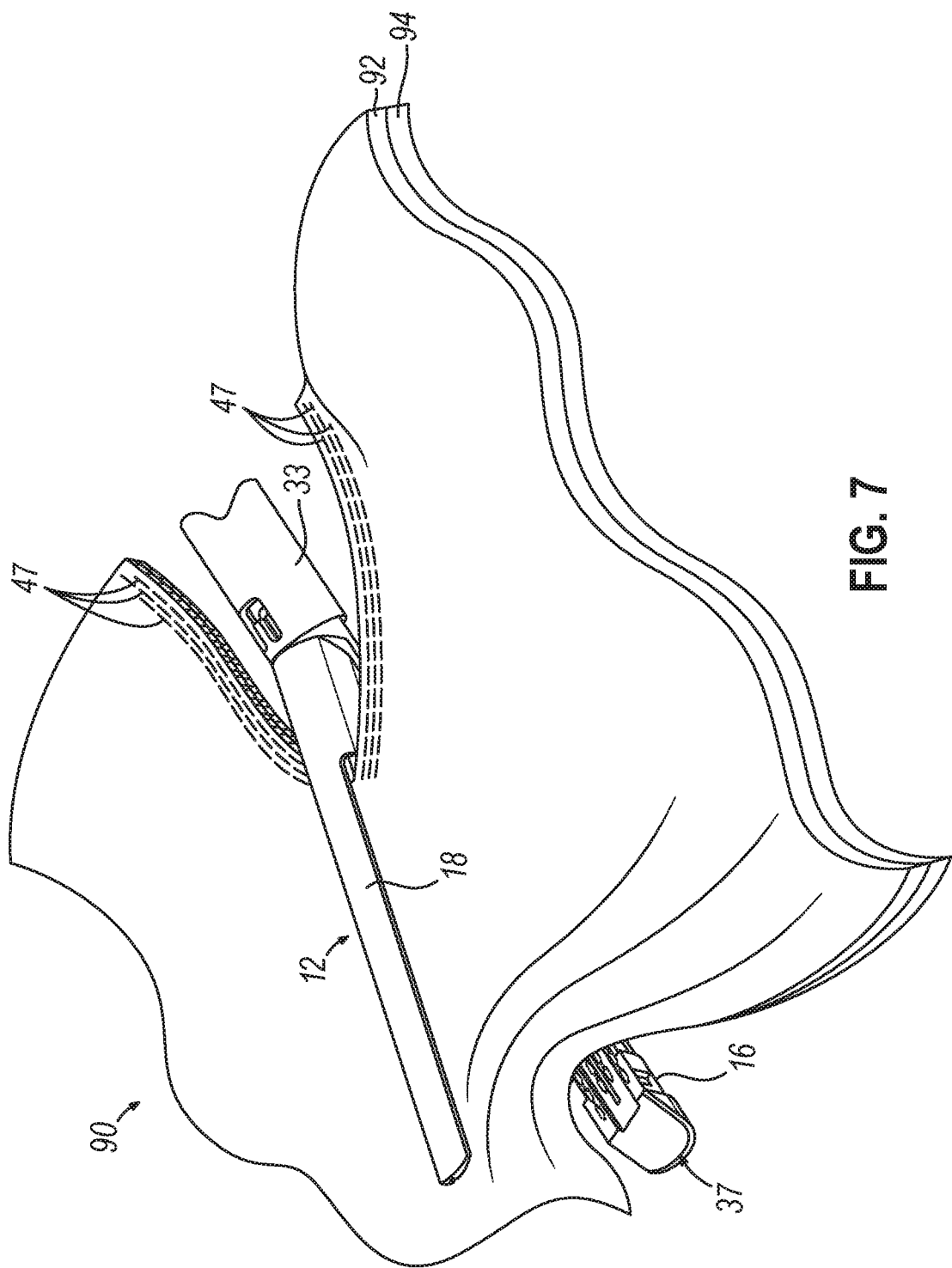
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Buttress Applier Cartridge

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
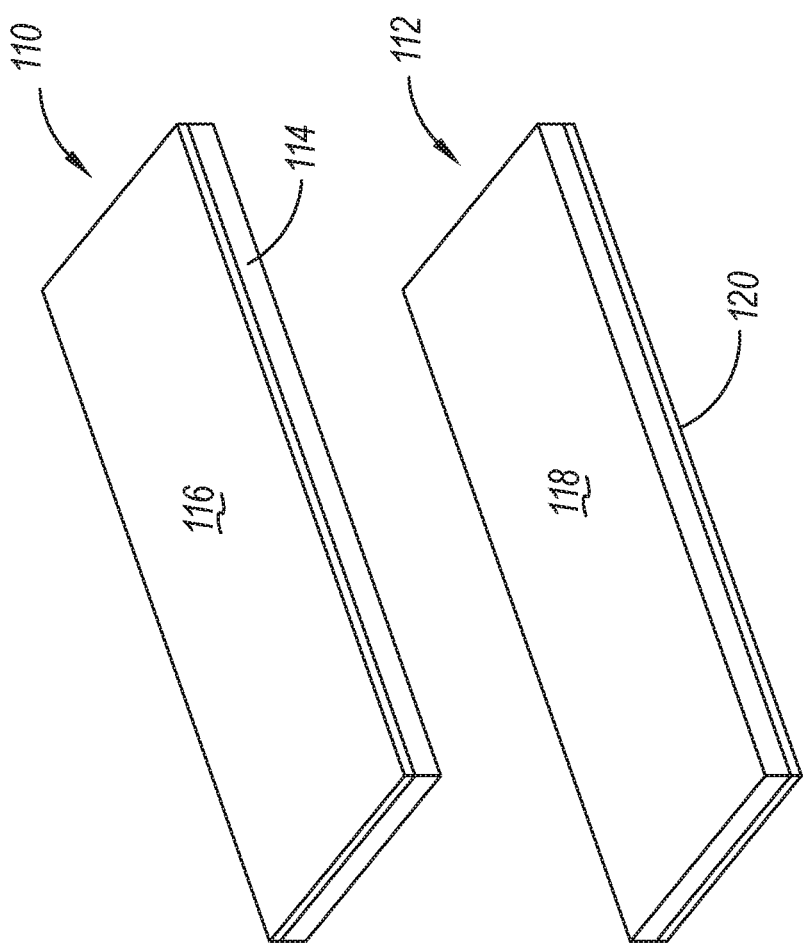
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
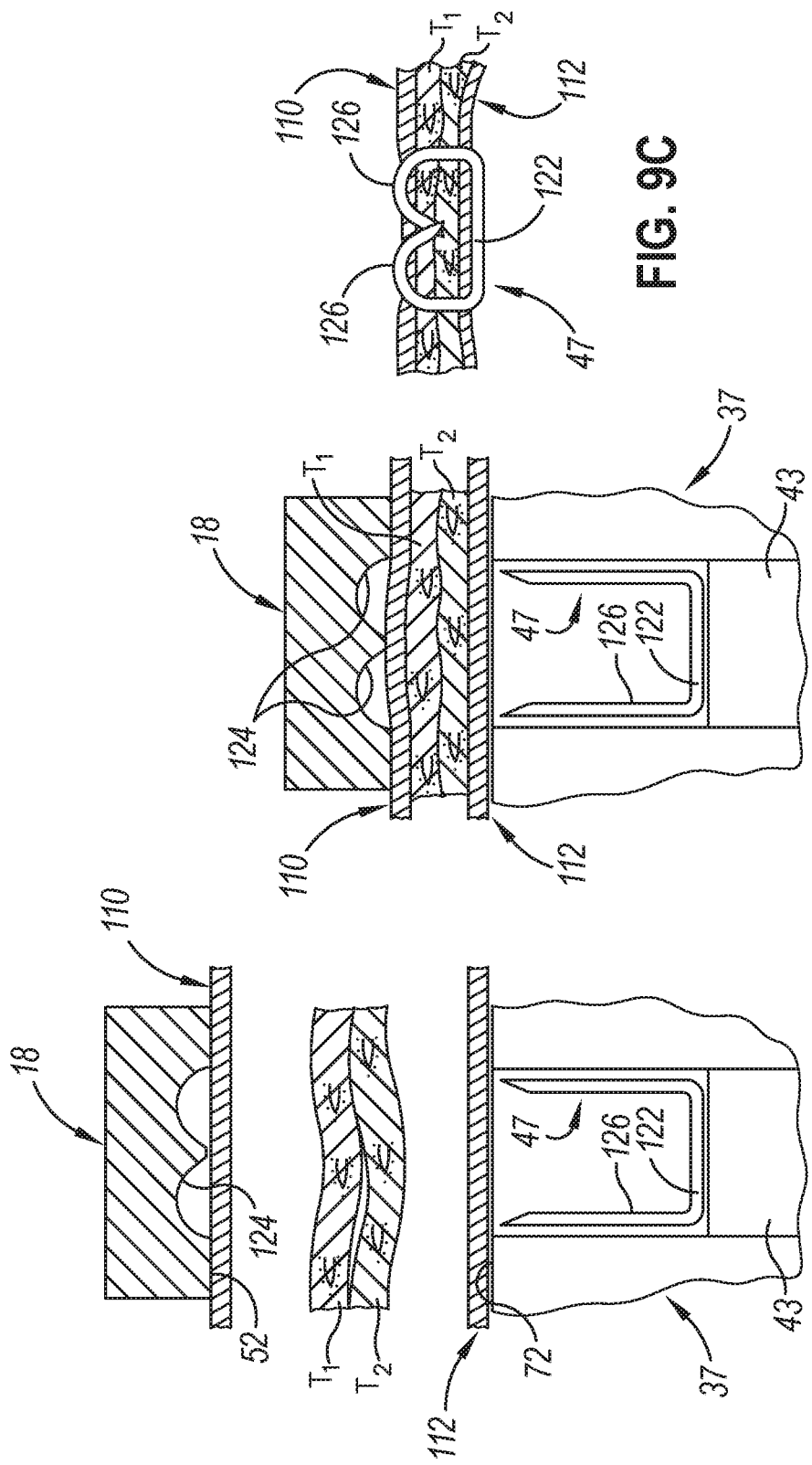
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional end view of a formed staple and the buttress assemblies of FIG. 9A after having been secured to the tissue by the end effector of FIG. 3.

FIGS. 9A-9C show an exemplary sequence in which surgical stapler end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in the open position. Buttress assembly (110) is adhered to underside (124) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
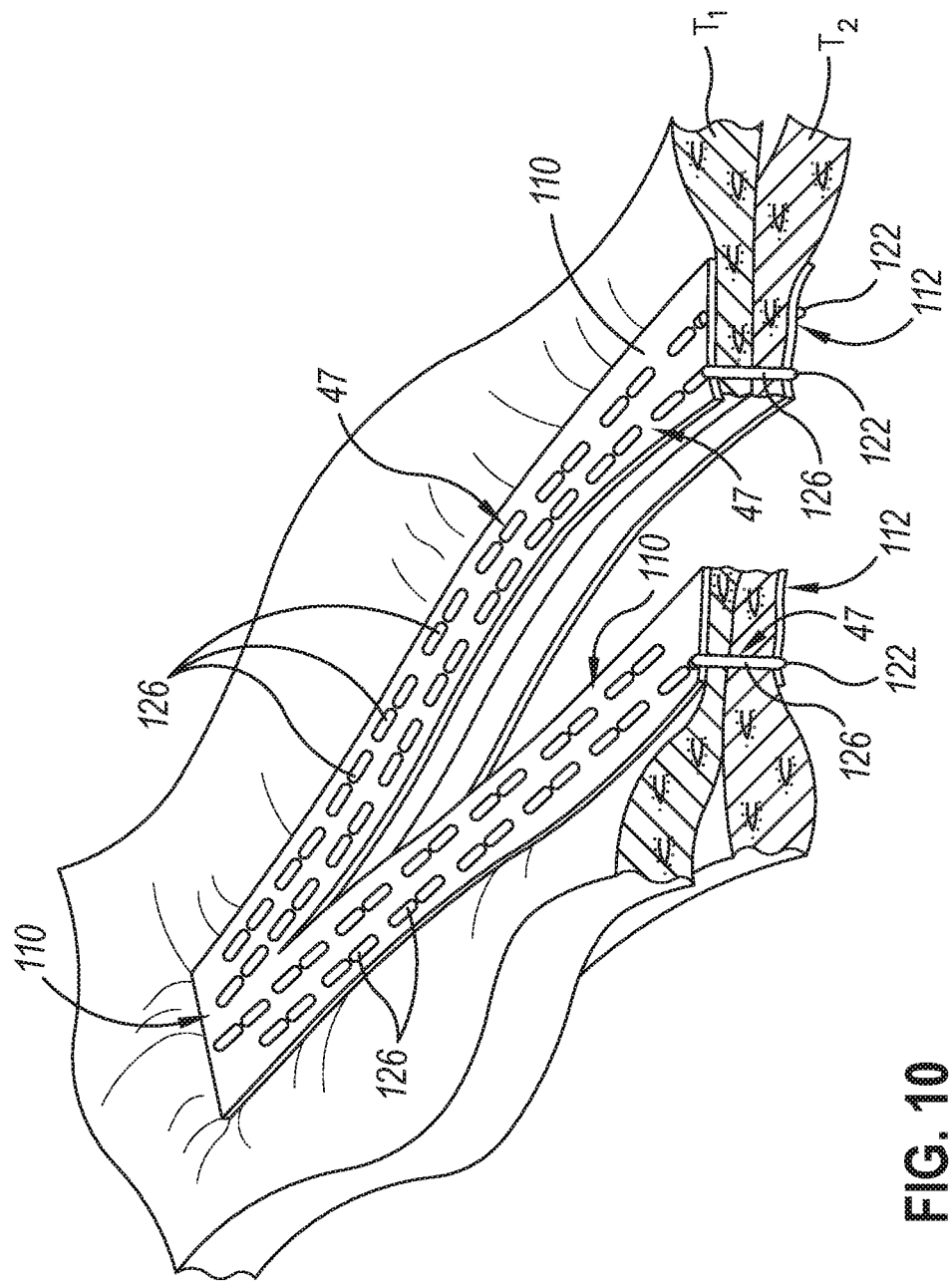
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttress assemblies (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress tissue assemblies (110, 112), separating each buttress assembly (110, 112) into a corresponding pair of sections, such that each section remains secured to a respective severed region of tissue ($T_1$, $T_2$).

C. Exemplary Buttress Applier Cartridge with Active Retainer Arms

Figure 11:
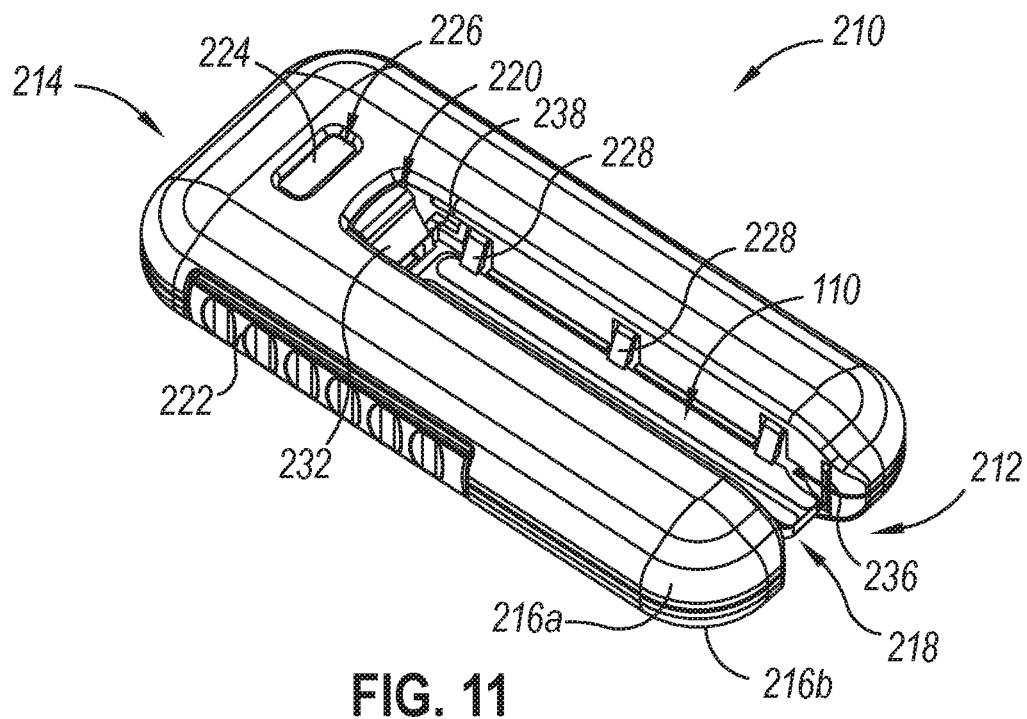
FIG. 11 depicts a perspective view of an exemplary buttress applier cartridge that may be used to carry and apply the buttress assemblies of FIG. 8.
Figure 12:
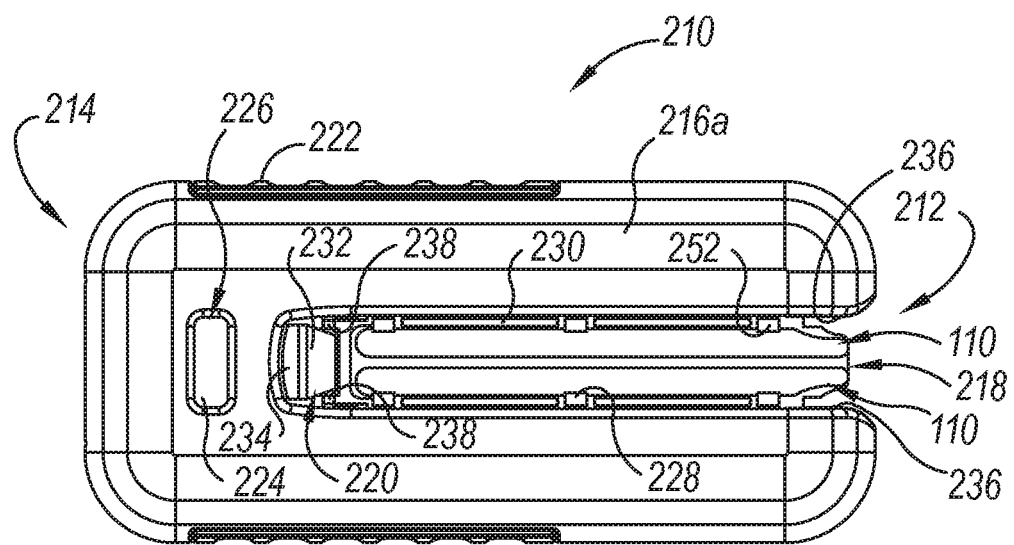
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto end effector jaws (16, 18) during that single surgical procedure. FIGS. 11-13B show an exemplary buttress applier cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, the outer edges of platform (218) include retention features (530) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Buttress applier cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
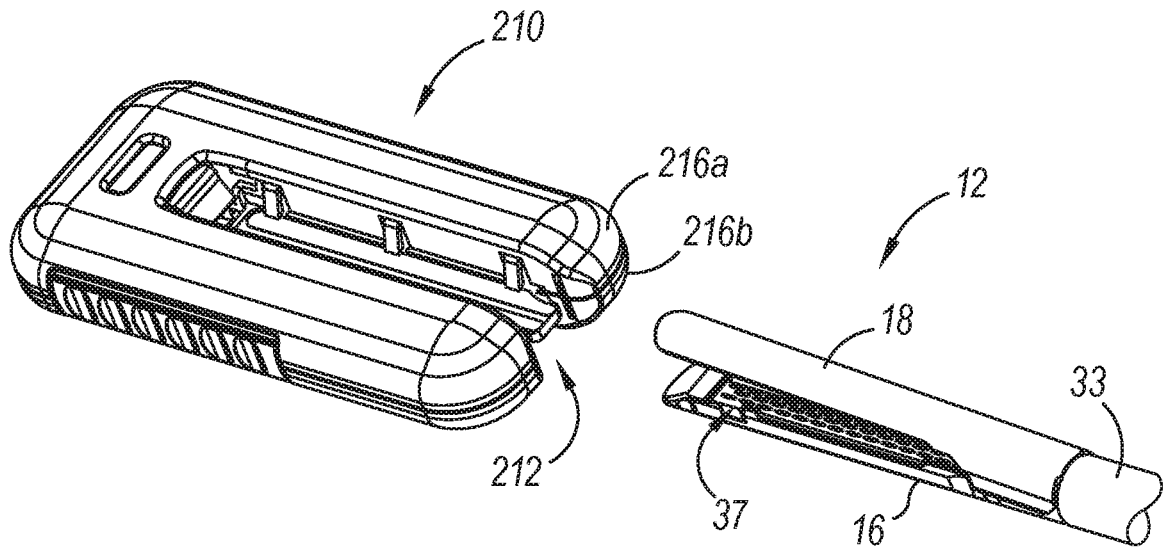
FIG. 13A depicts a perspective view of the end effector of FIG. 3 and the buttress applier cartridge of FIG. 11, showing the end effector and the buttress applier cartridge being aligned with one another.
Figure 13B:
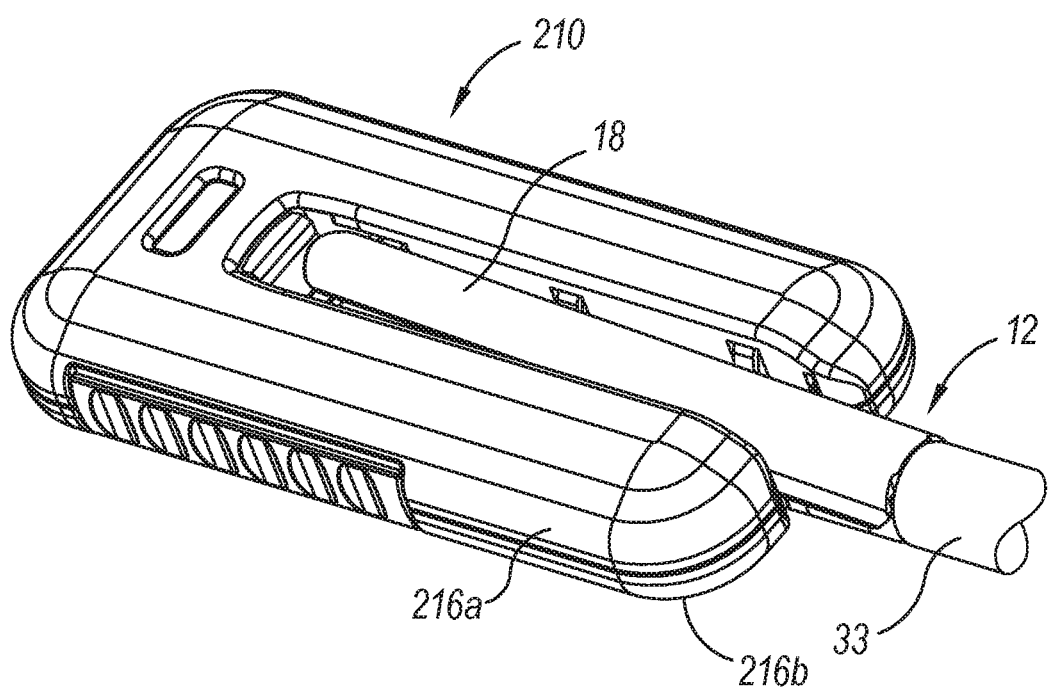
FIG. 13B depicts a perspective view of the end effector of FIG. 3 and the buttress applier cartridge of FIG. 11, with the end effectors jaws closed on a platform of the buttress applier cartridge.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG. 13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close end effector jaws (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that end effector jaws (16, 18) may be disengaged from platform (218) while buttress assemblies (110, 112) remain adhered to anvil (18) and staple cartridge (37).

III. Exemplary Alternative Applicator Devices and Related Methods of Applying a Buttress to a Surgical Stapler End Effector In some instances, it may be desirable to provide an applicator device that is configured to apply a staple reinforcing adjunct element to one or both jaws of a surgical stapler end effector (12) while the jaws remain in an open state, or otherwise without closing the jaws via actuation of the stapler's end effector (12) closure system, such as via actuation of closure trigger (26) of surgical stapler (10). Additionally, it may be beneficial to apply the adjunct material separately to the one or both jaws of the end effector (12) of surgical stapler (10). The exemplary applicator devices (310, 410, 510, 610, 710, 810) described below provide such functionality, such that applicator devices (310, 410, 510, 610, 710, 810) are configured to be manipulated relative to an end effector (12) to apply the adjunct material separately to one or both jaws without requiring actuated closure of the jaws like that shown in FIGS. 13A-13B described above. Applicator devices (310, 410, 510, 610, 710, 810) may apply a minimum pressure to appropriately seat the adjunct material against the desired jaw (e.g., lower jaw (16) or anvil (18)).

It will be appreciated that any of the exemplary applicator devices described below may be configured to apply an adjunct material in the form of a buttress, such as buttress assemblies (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector (12) jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

A. First Exemplary Alternative Applicator Device

Figure 14:
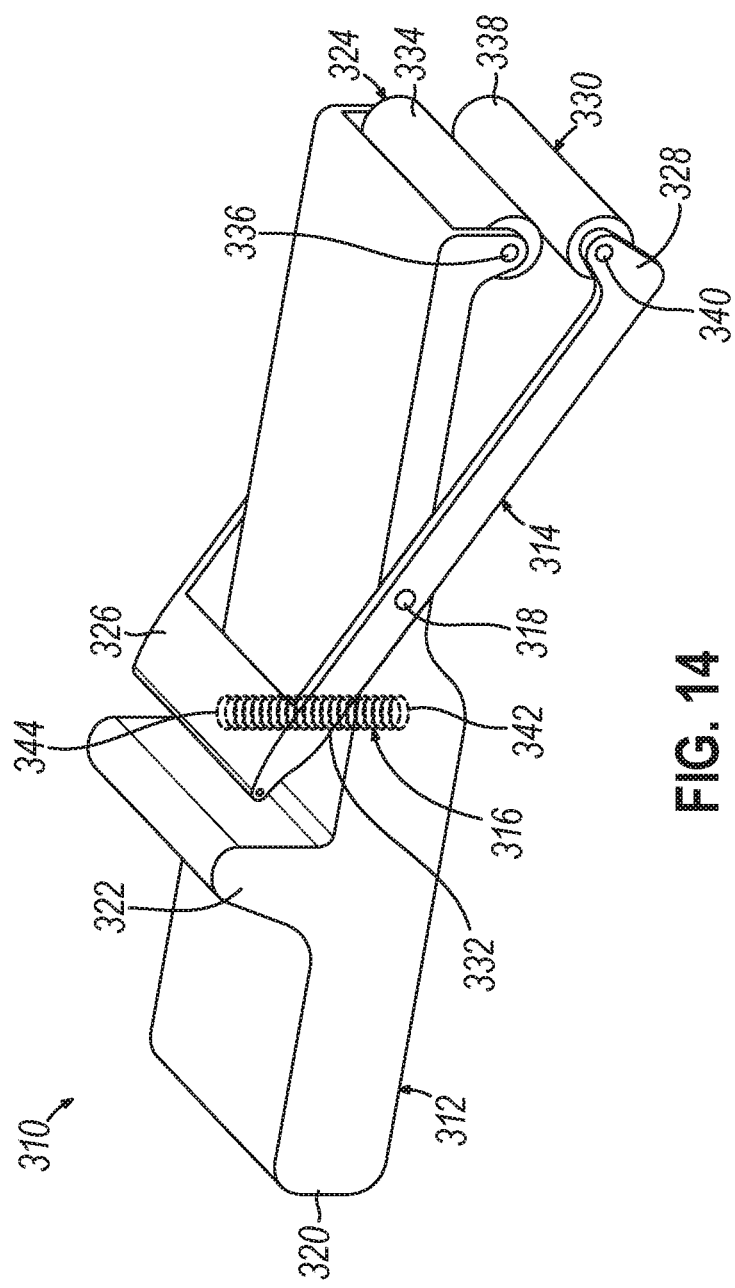
FIG. 14 depicts a perspective view of a first exemplary alternative applicator device.
Figure 15A:
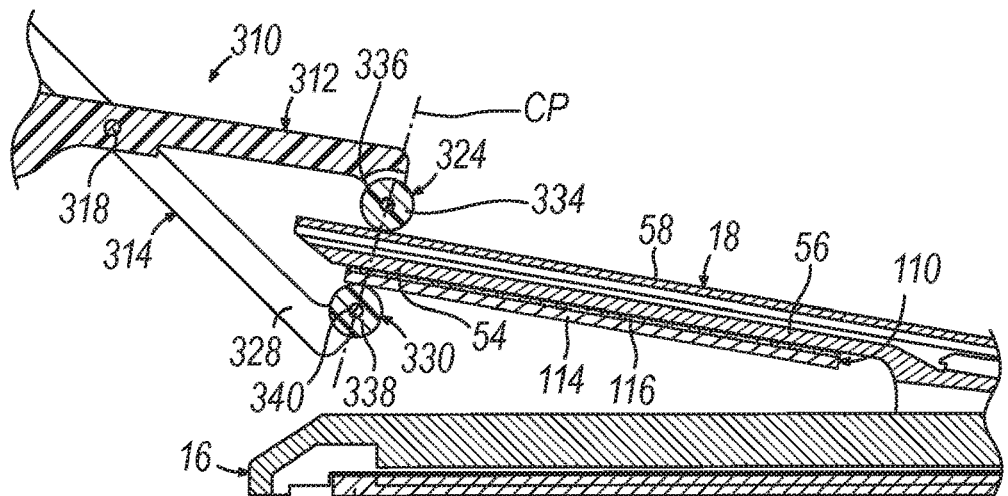
FIG. 15A depicts a cross-sectional view of the applicator device of FIG. 14, the buttress assembly of FIG. 8, and the end effector of FIG. 3, with the applicator device securing an already applied buttress assembly to a distal portion of an upper jaw of the end effector.
Figure 15B:
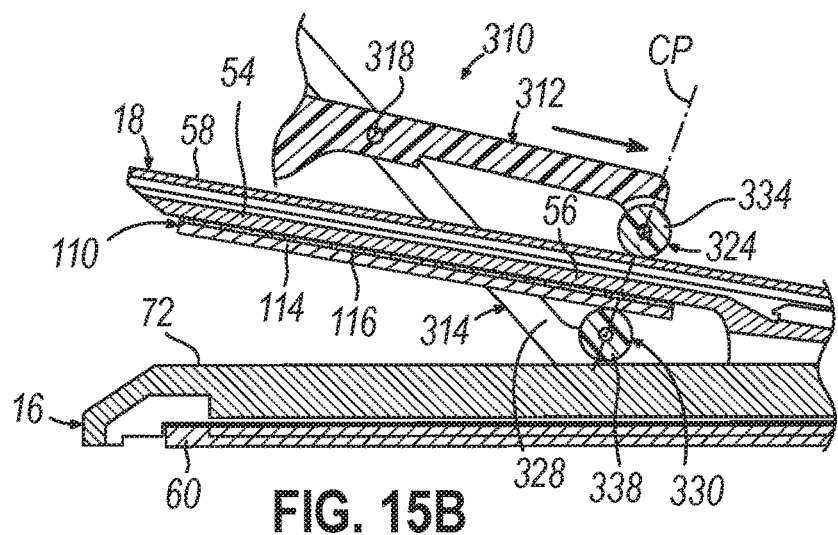
FIG. 15B depicts a cross-sectional view of the applicator device, the buttress assembly, and the end effector of FIG. 15A, with the applicator device securing the already applied the buttress assembly to a proximal portion of the upper jaw.
Figure 15C:
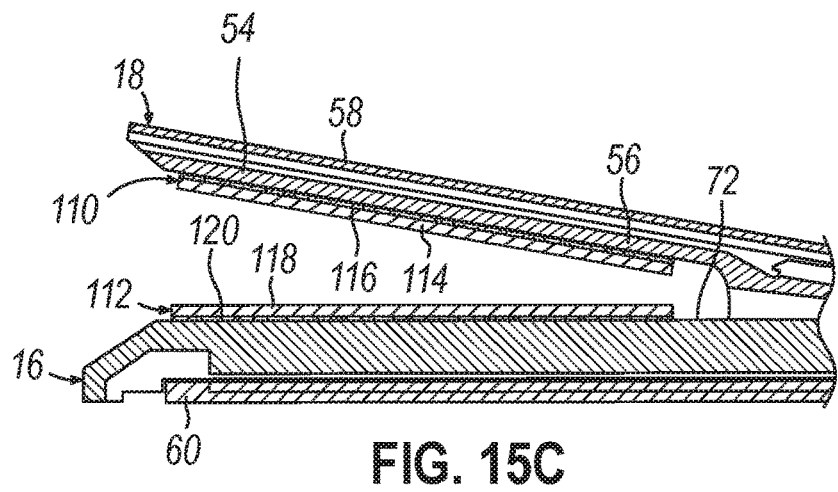
FIG. 15C depicts a cross-sectional view of the end effector of FIG. 15B, with the buttress assembly secured to the upper jaw and a second buttress assembly of FIG. 8 secured to a lower jaw of the end effector.

FIGS. 14-15C show a first exemplary alternative applicator device (310) that is configured to apply an adjunct material (e.g., buttress assembly (110, 112) or a tissue thickness compensator) to a jaw (e.g., lower jaw (16) or anvil (18)) of end effector (12) of surgical stapler (10). Applicator device (310) adjusts for the thickness of anvil (18) or lower jaw (16) allowing applicator device (310) to suitably apply adjunct material to both anvil (18) and lower jaw (16) separately. As shown in FIG. 14, applicator device (310) includes a housing (312), an arm (314), a resilient feature (316), and a coupling feature (shown as a pin (318)). Housing (312) includes a body member (320), a projection (322) extending from body member (320), and a first contact feature (324). First contact feature (324) may extend from body member (320) and is translatably fixed relative to body member (320). Arm (314) may be coupled with housing (312) using pin (318) that extends through a cavity (not shown) disposed in body member (320) of housing (312). However, other suitable structures for coupling housing (312) and arm (314) are also envisioned. Arm (314) includes proximal and distal ends (326, 328), with a second contact feature (330) disposed at distal end (328) of arm (314).

As shown in FIG. 14, resilient feature (316) may be coupled with body member (320) of housing (312) and proximal end (326) of arm (314). Arm (314) may be rotatably biased toward housing (312) using resilient feature (316) and pin (318). Resilient feature (316) is configured to bias arm (314), including second contact feature (330), relative to first contact feature (324) to apply a compression force as shown in FIGS. 15A-15B to secure the adjunct material to the desired jaw. Resilient feature (316) may include at least one spring operatively coupled with housing (312). As shown in FIG. 14, resilient feature (316) includes a tension spring (332). A first end (342) of tension spring (332) may be coupled with body member (320) and a second end (344) of tension spring (332) may be coupled with proximal end (326) of arm (314). Tension spring (332) may bias arm (314), including second contact feature (330), relative to first contact feature (324) by applying a compression force. FIG. 14 shows first and second contact features (324, 330) being separated by a distance from one another in a neutral configuration (i.e., a resting configuration). Alternatively, it is envisioned that second contact feature (330) may contact first contact feature (324) in the neutral configuration, so as to apply a predetermined contact force against first contact feature (324) prior to applicator device (310) being used to secure the adjunct material to the jaw of end effector (12).

First contact feature (324) and/or second contact feature (330) may include a roller. As shown in FIG. 14, first contact feature (324) includes a roller (334) that is coupled with body member (320) using a coupling feature (336). Similarly, second contact feature (330) includes a roller (338) that is coupled with arm (314) using a coupling feature (340). Rollers (334, 338) are configured to apply a compression force as rollers (334, 338) move along jaw. Particularly, roller (338) applies a compression force against a jaw of end effector (12), while roller (334) applies a counter force. As a result, roller (334) may be static and not deflect relative to body member (320). While rollers (334, 338) are shown as single elongate rollers in FIG. 14, other suitable rollers including rollers having a discontinuous contact surface are also envisioned. Coupling features (336, 340) may include, for example, a pin or another suitable coupling along feature that allows for rotation of roller (334) relative to body member (320) and rotation of roller (338) relative to arm (314). While first and second contact features (324, 330) are shown as including rollers (334, 338), it is also envisioned that first and second contact features (324, 330) may include low-friction elements that may slide along the adjunct material or the outer surface of the jaw.

FIGS. 15A-15C show the adjunct material being secured onto a stapling surface of a jaw of end effector (12). As described above, the adjunct material may include buttress assemblies (110, 112), tissue thickness compensators, or other suitable materials. The stapling surface is intended to include upper deck (72) of staple cartridge (37) that includes staple apertures (50) or a contact surface (52) of anvil (18) that includes staple forming pockets (53) as shown in FIG. 3. It is also envisioned that anvil (18) may be disposed on the lower jaw and the staple cartridge (37) may be disposed on the upper jaw. Applicator device (310) is shown as securing buttress assembly (110) to anvil (18), where buttress assembly (110) is already at least partially disposed on anvil (18). In some versions, a user utilizing a separate device (not shown) may initially apply buttress assembly (110) to anvil (18), so that applicator device (310) more securely presses buttress assembly (110) against anvil (18) to secure buttress assembly (110) in place using a desired pressure. In other versions, applicator device (310) may include or be coupled with a material dispenser that supplies the adjunct material, similar to material dispenser (430) which is described in detail below with reference to FIGS. 16-17B.

FIG. 15A shows a cross-sectional view of applicator device (310) of FIG. 14 and end effector (12) of FIG. 3, with applicator device (310) securing buttress assembly (110) to a distal portion (54) of anvil (18) of end effector (12). As described above, buttress assembly (110) includes upper adhesive layer (116) that is configured to adhere buttress assembly (110), including buttress body (114), to contact surface (52) of anvil (18). As shown in FIG. 15A, anvil (18) includes an outer surface (58) disposed 180 degrees opposite contact surface (52). Roller (338) of second contact feature (330) is configured to apply a compression force to pinch buttress assembly (110) against distal portion (54) of anvil (18) to secure upper adhesive layer (116) of buttress assembly (110) with contact surface (52), which secures upper adhesive layer (116) to contact surface (52). As shown in FIG. 15A-15B, rollers (334, 338) are disposed opposite one another along a compression plane (CP). Roller (334) may rotate in an opposite direction relative to roller (338). Roller (338) applies a compression force as roller (334) moves along outer surface (58) of anvil (18) and roller (338) moves along contact surface (52) of anvil (18). In some versions, roller (338) may apply the compression force as roller (334) moves along contact surface (52) of anvil (18) and roller (338) moves along outer surface (58) of anvil (18).

FIG. 15B shows a cross-sectional view of applicator device (310) and end effector (12) of FIG. 15A, with applicator device (310) applying buttress assembly (110) to a proximal end (54) of anvil (18) after roller (334) rolls along outer surface (58) of anvil (18) and roller (338) rolls along buttress body (114) to adhere upper adhesive layer (116) with contact surface (52). While the user may generally secure buttress assembly (110) to distal portion (54) of anvil (18) then secure buttress assembly (110) to proximal portion (56) of anvil (18), it is also envisioned that the user may secure buttress assembly (110) to proximal portion (56) of anvil (18) then secure buttress assembly (110) to distal portion (54) of anvil (18).

FIG. 15C shows a cross-sectional view of end effector (12) of FIG. 15B, with buttress assembly (110) secured to contact surface (52) of anvil (18) and buttress assembly (112) secured to upper deck (72) of lower jaw (16) of end effector (12). As shown, buttress assembly (112) includes lower adhesive layer (120) that is configured to adhere buttress assembly (112), including buttress body (118), to upper deck (72) of lower jaw (16). The application of buttress assembly (112) may be similar to the application of buttress assembly (110) described above. For example, roller (338) may apply a compression force as roller (334) moves along outer surface (60) of lower jaw (16) and roller (338) moves buttress body (118) to adhere lower adhesive layer (120) with upper deck (72) of lower jaw (16). However, it is also envisioned that roller (338) may apply the compression force as roller (334) moves along buttress body (114) to adhere lower adhesive layer (120) with upper deck (72) of lower jaw (16) and roller (338) moves along outer surface (60) of lower jaw (16). Since lower jaw (16) is shown as being thicker than anvil (18), to spread rollers (334, 338) further apart, tension spring (332) may be stretched further. Stretching tension spring (332) may result in a greater spring force so that lower jaw (16) is interposed between rollers (334, 338).

B. Second Exemplary Alternative Applicator Device

Figure 16:
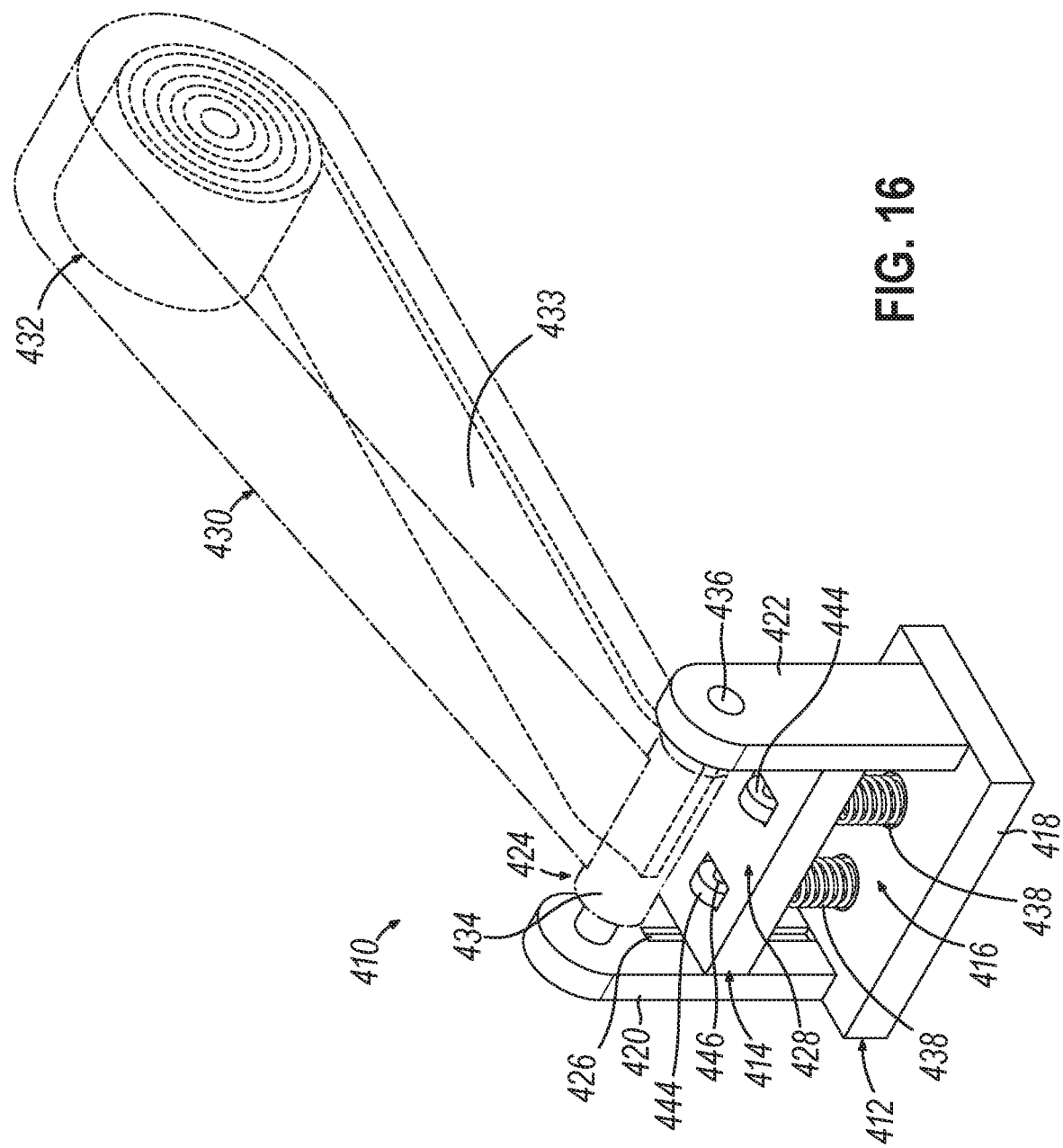
FIG. 16 depicts a perspective view of a second exemplary alternative applicator device, with select internal components being shown schematically in phantom.
Figure 17A:
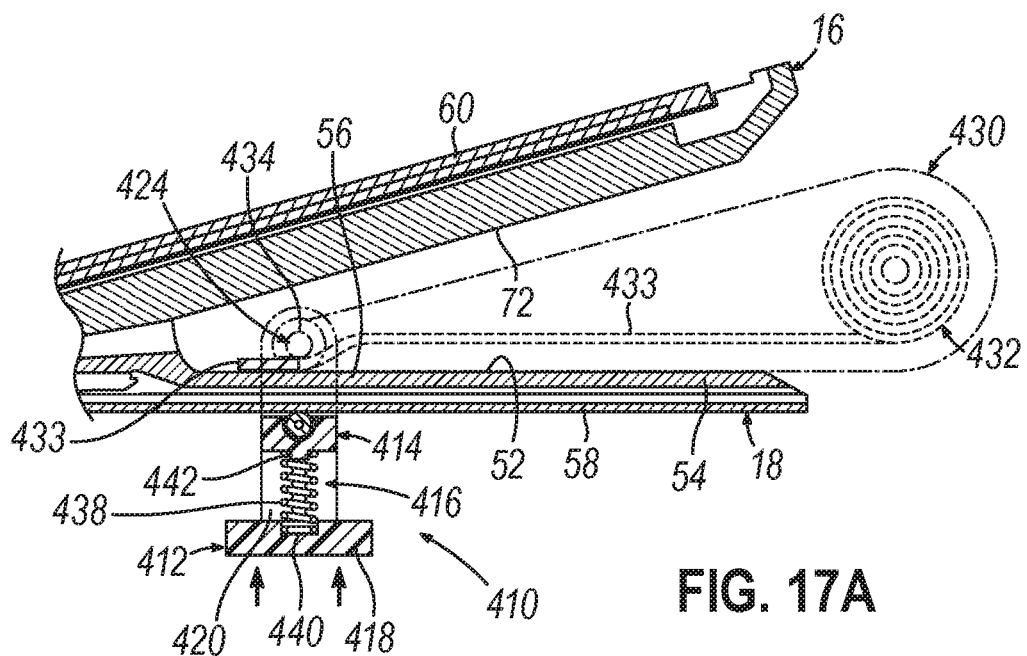
FIG. 17A depicts a cross-sectional view of the applicator device of FIG. 16 and the end effector of FIG. 3, with the applicator device applying and securing a continuous buttress assembly from a material dispenser to a proximal portion of the upper jaw of the end effector.
Figure 17B:
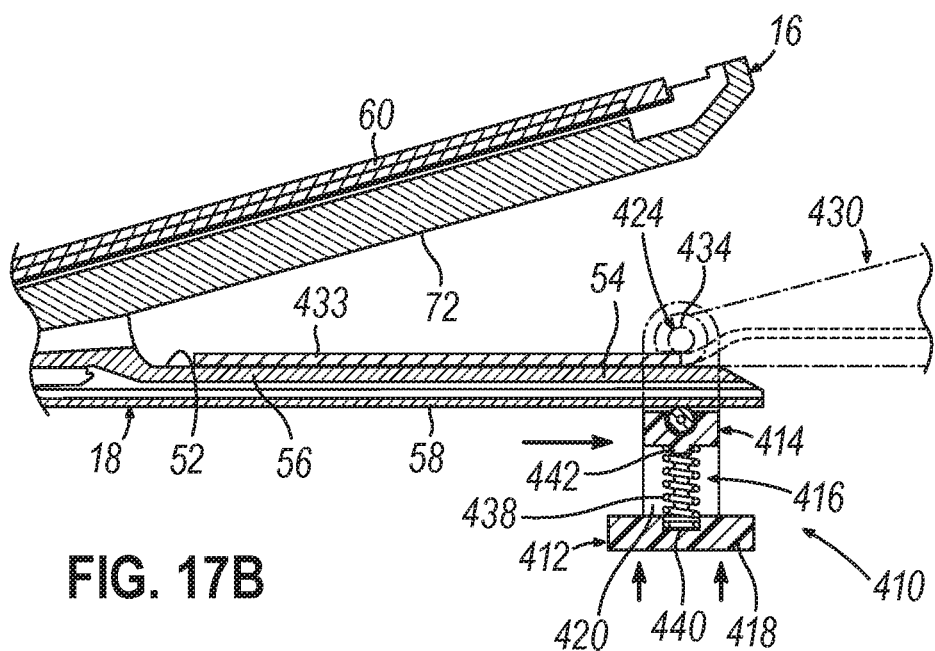
FIG. 17B depicts a cross-sectional view of the applicator device and the end effector of FIG. 17A, with the applicator device applying and securing the continuous buttress assembly from the material dispenser to a distal portion of the upper jaw.

FIGS. 16-17B show a second exemplary alternative applicator device (410) that is configured to apply an adjunct material to a jaw (e.g., lower jaw (16) or anvil (18)) of end effector (12) of surgical stapler (10). Applicator device (410) adjusts for thickness of anvil (18) or lower jaw (16) allowing applicator device (410) to suitably apply adjunct material to anvil (18) and lower jaw (16). As a result, the application of buttress assembly (112) using applicator device (410) to lower jaw (16) that includes staple cartridge (37) may be similar to the application of buttress assembly (110) described above. As shown in FIG. 16, applicator device (410) includes a housing (412), an arm (414), and a resilient feature (416). Housing (412) includes a base (418), a first upright (420), a second upright (422), and a first contact feature (424). First and second uprights (420, 422) extend outwardly from base (418). First and second uprights (420, 422) are shown as parallel to one another. Optionally, arm (414) may translate along slots (426) disposed in first and second uprights (420, 422). Arm (414) includes a second contact feature (428).

Housing (412) may include an adjunct material dispenser (430) that dispenses adjunct material from a spool (432) using first contact feature (424). As shown, the adjunct material is a continuous buttress assembly (433). Buttress assembly (433) may include an adhesive surface to couple with the stapling surface. It will be appreciated that material dispenser (430) may be further configured and operable in accordance with the teachings of U.S. Pat. Pub. No. 2015/0076212, entitled "Surgical End Effector Having Buttress Retention Features," published Mar. 19, 2015, the disclosure of which is incorporated by reference herein. Continuous buttress assembly (433) may be dispensed at first contact feature (424). First contact feature (424) applies buttress assembly (433) to contact surface (52). As shown, first contact feature (424) includes a roller (434) that is secured with first and second uprights (420, 422) and material dispenser (430) using a coupling feature (436). Optionally, spool (432) may be removed from housing (412) by removing coupling feature (436) that couples first contact feature (424) with material dispenser (430). Material dispenser (430) may deliver multiple buttresses without reloading. Additionally, material dispenser (430), utilizing a single product code, may dispense buttresses having varying lengths. This may reduce the number of different buttress sizes that the user has stock or otherwise have on hand.

Applicator device (410) may control the force with which the adjunct material is applied to the jaw from material dispenser (430) using resilient feature (416). Resilient feature (416) may be disposed between base (418) of housing (412) and arm (414). Resilient feature (416) may be configured to bias arm (414), including second contact feature (428), relative to first contact feature (424) to apply a compression force as shown in FIG. 17A-17B. Arm (414) is configured to translate relative to base (418) using resilient feature (416). For example, resilient feature (416) may include at least one spring. As shown in FIG. 16, resilient feature (416) includes a pair of compression springs (438). However, more or fewer compression springs (438), such as a single compression spring, is also envisioned.

As shown in FIGS. 17A-17B, first ends (440) of compression springs (438) may be coupled with base (418) and second ends (442) of compression springs (438) may be coupled with arm (414). Compression spring (438) is configured to bias arm (414), including second contact feature (428), relative to first contact feature (424) by applying a compression force. In other words, compression springs (438) push arm (414) upward onto outer surface (58) of anvil (18). Compression springs (438) disposed between arm (414) and base (418) may provide the desired application pressure to secure the adjunct material with the stapling surface of the jaw. FIG. 16 shows first and second contact features (424, 428) being separated by a distance from one another in a neutral configuration (i.e., a resting configuration). Alternatively, it is envisioned that second contact feature (428) may contact first contact feature (424) in the neutral configuration, so as to apply a predetermined contact force against first contact feature (424) prior to applicator device (410) being used to secure the adjunct material to upper deck (72) of lower jaw (16) or to contact surface (52) of anvil (18).

First contact feature (424) and/or second contact feature (428) may include a roller. As shown in FIG. 16, second contact feature (428) includes a pair of rollers (444) configured to apply a compression force as rollers (444) move along the outer surface of the jaw. While a pair of rollers (444) are shown, more or fewer rollers (444) are also envisioned. Rollers (444) of arm (414) allow smooth application of adjunct material along length of the jaw. Arm (414), including rollers (444), is configured to translate relative to base (418) to simultaneously contact outer surface as spool (432) applies adjunct material to upper deck (72) of lower jaw (16) or to contact surface (52) of anvil (18). Rollers (444) may be coupled with arm (414) using a coupling feature (446). Particularly, roller (444) is configured to apply a compression force against a jaw of end effector (12), while roller (434) is configured to apply a counter force. As a result, roller (434) may be static and not deflect relative to base (418). As shown in FIG. 14, rollers (434, 444) are disposed opposite one another along a compression plane (CP). While roller (434) is shown as a single elongate roller in FIG. 16, other rollers are also envisioned including rollers having a discontinuous contact surfaces or multiple discrete rollers. Coupling features (436, 446) may include, for example, a pin or another suitable coupling along feature that allows for rotation of roller (434) relative to material dispenser (430) and rotation of roller (444) relative to arm (414). While second contact feature (428) is shown as including rollers (444), it is also envisioned that second contact feature (428) may include a low-friction element that may slide along the jaw.

FIGS. 17A-17B show an adjunct material being applied and secured onto a stapling surface of a jaw of end effector (12). Particularly, FIG. 17A shows a cross-sectional view of applicator device (410) of FIG. 16 and end effector (12) of FIG. 3, with applicator device (410) securing buttress assembly (110) to a proximal portion (56) of anvil (18). As shown, buttress assembly (110) includes upper adhesive layer (116) that is configured to adhere buttress assembly (110), including buttress body (114), to contact surface (52) of anvil (18). Outer surface (58) of anvil (18) is disposed 180 degrees opposite contact surface (52). As shown in FIG. 17A, rollers (444) of second contact feature (428) apply a compression force to pinch buttress assembly (110) against proximal portion (56) of anvil (18) to secure upper adhesive layer (116) of buttress assembly (110) to contact surface (52). Roller (434) may rotate in an opposite direction relative to rollers (444). Rollers (444) apply the compression force as roller (434) moves along outer surface (58) of anvil (18) and roller (434) moves along buttress body (114) to adhere upper adhesive layer (116) with contact surface (52) of anvil (18). Applicator device (410) exerts a clamping force on anvil (18) between proximal tip of roller (434) and a central point of rollers (444) of arm (414) that serves as a bottom force limiting backstop device.

FIG. 17B shows a cross-sectional view of applicator device (410) and end effector (12) of FIG. 17A, with applicator device (410) applying and securing buttress assembly (110) to distal portion (54) of anvil (18) after roller (434) rolled along buttress body (114) to adhere upper adhesive layer (116) with contact surface (52) and rollers (444) rolled along outer surface (58) of anvil (18). While the user may generally secure buttress assembly (110) to proximal portion (56) of anvil (18) then secure buttress assembly (110) to distal portion (54) of anvil (18), it is envisioned that the user may secure buttress assembly (110) to distal portion (54) of anvil (18) then secure buttress assembly (110) to proximal portion (56) of anvil (18). The application of buttress assembly (112) to lower jaw (16) that includes staple cartridge (37) may be similar to the application of buttress assembly (110) described above.

C. Third Exemplary Alternative Applicator Device

Figure 18:
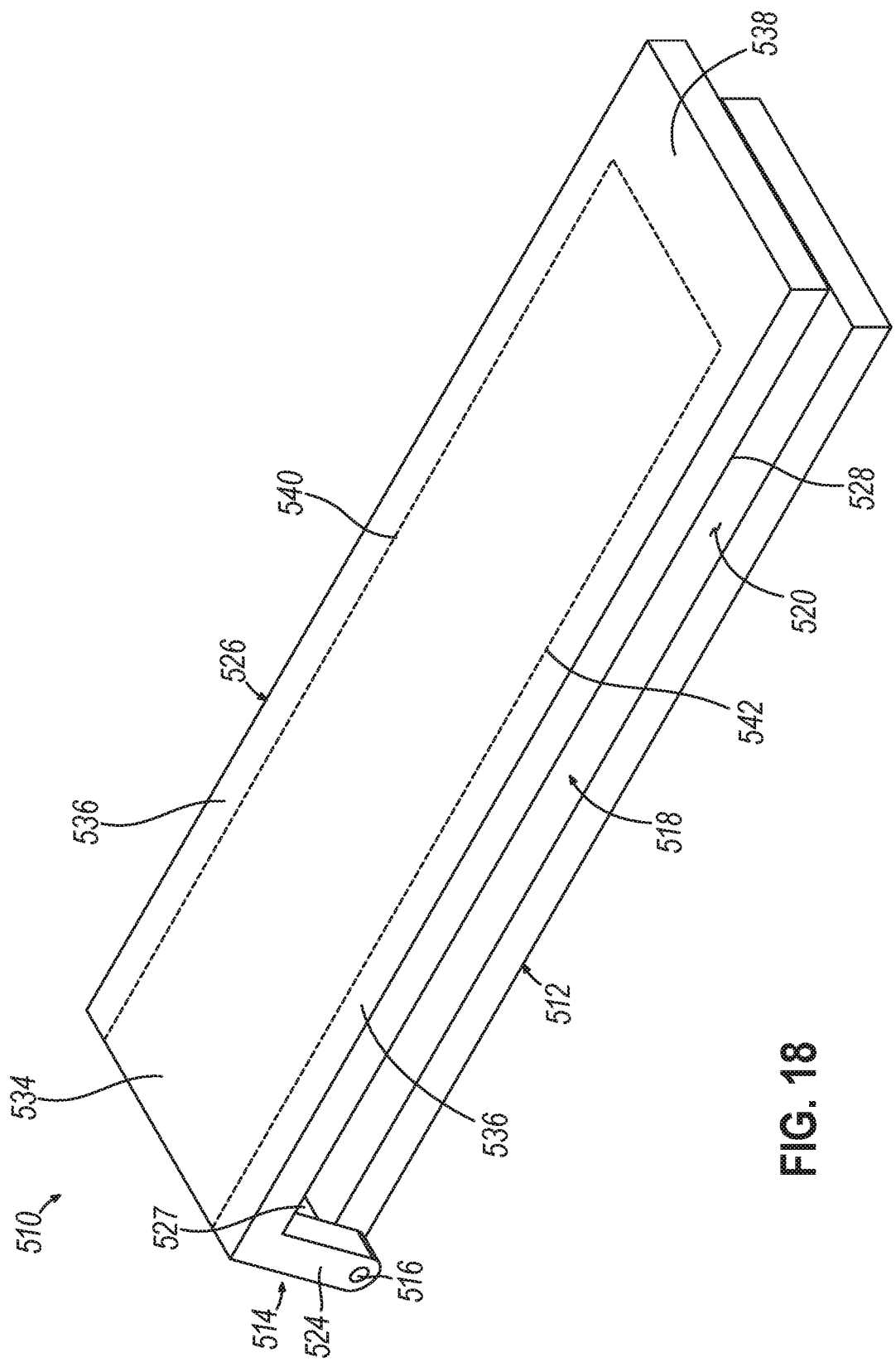
FIG. 18 depicts a perspective view of a third exemplary alternative applicator device.
Figure 19A:
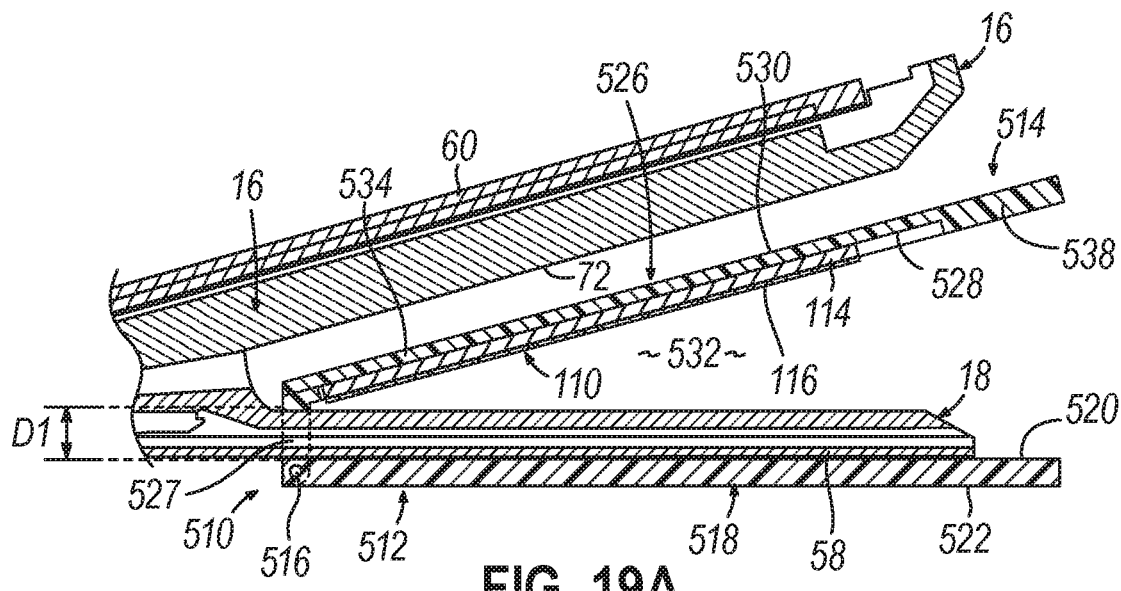
FIG. 19A depicts a cross-sectional view of the applicator device of FIG. 18, the buttress assembly of FIG. 8, and the end effector of FIG. 3, with an arm of the applicator device pivoting toward the upper jaw.
Figure 19B:
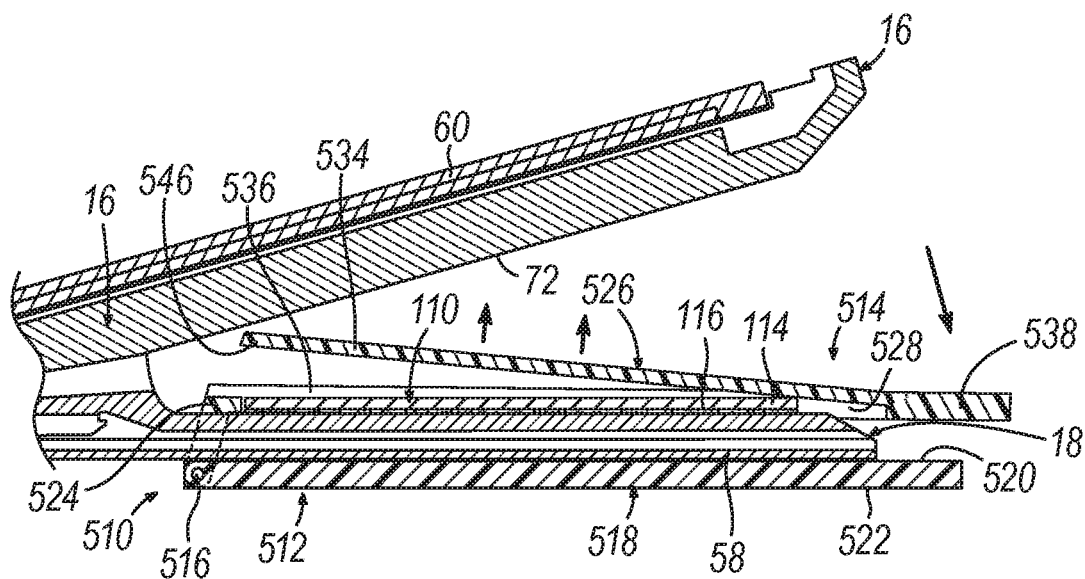
FIG. 19B depicts a cross-sectional view of the applicator device, the buttress assembly, and the end effector of FIG. 19A, with lateral frangible portions of the arm severing to release the buttress assembly from the applicator device and apply and secure the buttress assembly to the upper jaw.
Figure 19C:
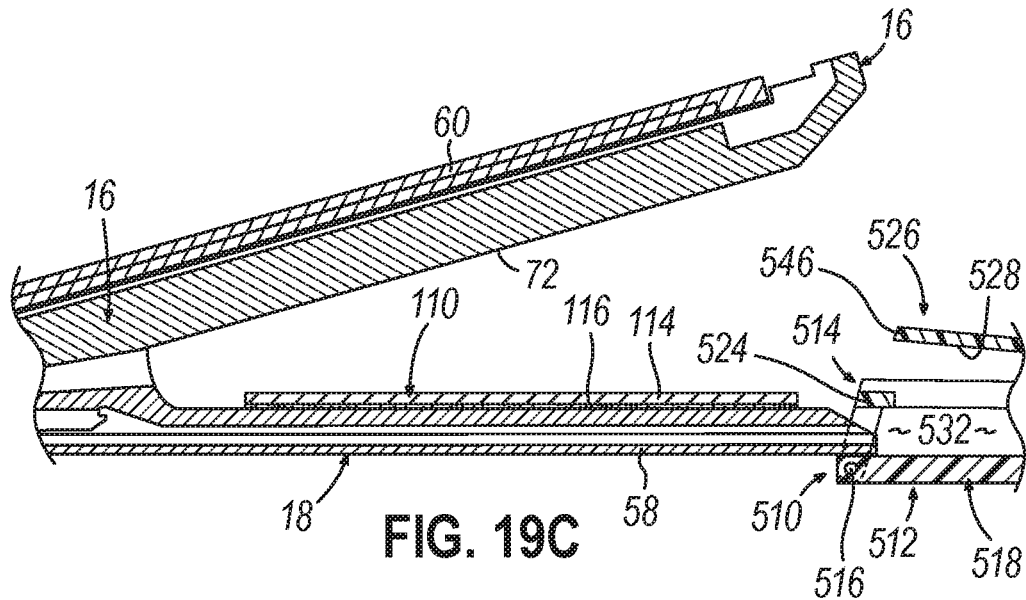
FIG. 19C depicts a cross-sectional view of the applicator device, the buttress assembly, and the end effector of FIG. 19A, with the buttress assembly secured to the upper jaw and the applicator device being removed from the upper jaw.

FIGS. 18-19C show a third exemplary alternative applicator device (510) that is configured to apply an adjunct material to a jaw (e.g., anvil (18)) of end effector (12) of surgical stapler (10). As shown in FIG. 18, applicator device (510) includes a housing (512), an arm (514), and a hinge (516). Hinge (516) pivotably couples arm (514) with housing (512) at a hinge point (HP), so that arm (514) may pivot relative to housing (512) to apply and secure the adjunct material (shown as buttress assembly (110)) to anvil (18). Housing (512) includes a first contact feature (518) that is shown as a generally planar base. First contact feature (518) includes inner and outer surfaces (520, 522), with inner surface (520) facing arm (514). Arm (514) includes a connecting portion (524) and a second contact feature (526) that is shown as a generally planar platform. Connecting portion (524) has a first thickness (D1) to accommodate the thickness of anvil (18). Connecting portion (524) may include an aperture (527) to allow the jaw to extend therethrough as shown in FIGS. 19A-19C. Second contact feature (526) includes inner and outer surfaces (528, 530), with inner surface (528) facing inner surface (520) of first contact feature (518). As shown in FIGS. 19A-19B, a cavity (532) is disposed between inner surfaces (520, 528) of first and second contact feature (518, 526).

Second contact feature (526) is configured to pivot relative to first contact feature (518) between an open configuration (shown in FIG. 19A) and a closed configuration (shown in FIG. 19B) where second contact feature (526) pushes buttress assembly (110) into contact with the stapling surface. As shown in FIG. 18, second contact feature (526) includes inner and outer portions (534, 536) and a retaining portion (538). Inner and outer portions (534, 536) are connected together by lateral frangible portions (540, 542). Lateral frangible portions (540, 542) are configured to sever when a predetermined pressure is applied to release adjunct material from applicator device (510). Retaining portion (538) is disposed an end of second contact feature (526) disposed opposite to hinge (516). Lateral frangible portions (540, 542) are configured to break to separate inner and outer portions (534, 536), except for retaining portion (538) that keeps inner and outer portions (534, 536) coupled together.

FIGS. 19A-19B show adjunct material (shown as buttress assembly (110)) being secured onto the upper jaw (shown as anvil 18) of end effector (12). As shown, applicator device (510) may load and secure buttress assembly (110) to anvil (18). Particularly, FIG. 19A shows a cross-sectional view of applicator device (510) of FIG. 18 and end effector (12) of FIG. 3, with arm (514) of applicator device (510) pivoting toward an upper jaw (shown as anvil (18)). Outer surface (58) of anvil (18) is disposed 180 degrees opposite contact surface (52). As shown, buttress assembly (110) includes upper adhesive layer (116) that is configured to adhere buttress assembly (110), including buttress body (114), to contact surface (52) of anvil (18). As shown in FIG. 19A, second contact feature (526) of arm (514) provides an elongate platform that a first side of the buttress assembly (110) is releasably attached to (e.g., via adhesion). In other words, buttress body (114) may be temporarily attached to inner surface (528) of second contact feature (526) using an adhesive or a mechanical coupling feature. Inner portion (534) of second contact feature (526) may be perforated along the sides except for retaining portion (538).

FIG. 19B shows a cross-sectional view of applicator device (510) and end effector (12) of FIG. 19A, with lateral frangible portions (540, 542) breaking to release applicator device (510) from anvil (18). Second contact feature (526) applies a compression force to pinch buttress assembly (110) against proximal portion (56) of anvil (18) to apply and secure buttress assembly (110) to contact surface (52). When arm (514) is rotated toward and compressed against the end effector (12) jaw with sufficient force, lateral frangible portions (540, 542) sever. This transforms inner portion (534) into a flap (544) with a free end that remains hingedly attached to retaining portion (538) so that the remainder of arm (514), such as flap (544) is not a completely loose piece that may fall onto the patient or the floor. Retaining portion (538) may include a bendable portion that is configured to bend, but not break when buttress assembly (110) is released from applicator device (510) as shown in FIG. 19B. Buttress assembly (110) separates from inner portion (534) of second contact feature (526) in response to closure of the arm (514) on the end effector (12) jaw. As a result, applicator device (510) may control the force with which buttress assembly (110) is applied to contact surface (52) of anvil (18) using lateral frangible portions (540, 542).

Lateral frangible portions (540, 542) are shown as spaced perforations along respective sides of inner portion (534), but not at the distal end. For ease of application, lateral frangible portions (540, 542) may disposed around the area adjacent buttress assembly (110), so that when buttress assembly (110) is applied, lateral frangible portions (540, 542) tear and secure buttress assembly (110) to anvil (18). Lateral frangible portions (540, 542) may be altered to increase or decrease the force with which buttress assembly (110) is applied to anvil (18) prior to lateral frangible portions (540, 542) severing. For example, the spacing of adjacent perforations and/or the ratio of material to gaps may be altered. Lateral frangible portions (540, 542) on applicator device (510) may prevent re-use after deployment of the adjunct material. Applicator device (510) prevented from being re-used by the severed lateral frangible portions (540, 542). In some versions, arm (514) may destroys itself or lock into a non-closable state once arm (514) opens, such that the detent is overcome, but difficult to reset.

FIG. 19C shows a cross-sectional view of applicator device (510) and end effector (12) of FIG. 19B, with buttress assembly (110) applied to anvil (18) and applicator device (510) being actively removed. For example, applicator device (510) may be slid distally relative to end effector (12) using aperture disposed in arm (514).

D. Fourth Exemplary Alternative Applicator Device

Figure 20:
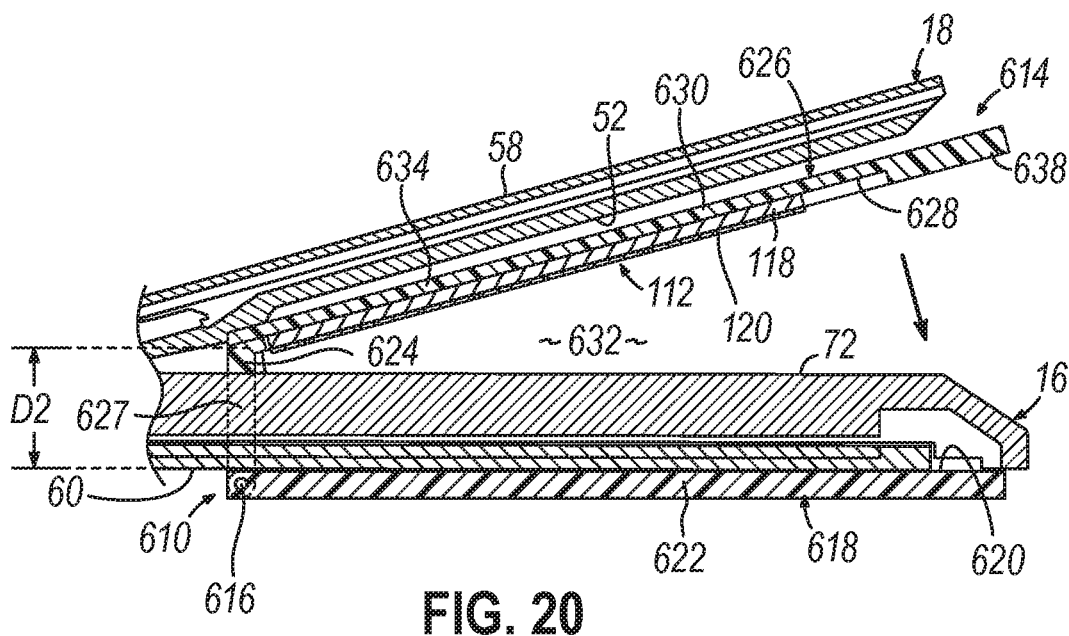
FIG. 20 depicts a cross-sectional view of a fourth exemplary applicator device, the buttress assembly of FIG. 8, and the end effector of FIG. 3, with an arm of the applicator device pivoting toward the lower jaw of the end effector.

FIG. 20 shows a fourth exemplary alternative applicator device (610) that is configured to apply an adjunct material to a jaw (e.g., lower jaw (16)) of end effector (12) of surgical stapler (10). As shown, applicator device (610) includes a housing (612), an arm (614), and a hinge (616). Hinge (616) pivotably couples arm (614) with housing (612) at a hinge point, so that arm (614) may pivot relative to housing (612) to apply and secure the adjunct material (shown as buttress assembly (112)) to lower jaw (16). Housing (612) includes a first contact feature (618) that is shown as a generally planar base. First contact feature (618) includes inner and outer surfaces (620, 622), with inner surface (620) facing arm (614).

Arm (614) includes a connecting portion (624) and a second contact feature (626) that is shown as a generally planar platform. Connecting portion (624) has a second thickness (D2) to accommodate the thickness of lower jaw 16). As a result, connecting portion (624) may be longer than connecting portion (524), so as to account for the increased thickness (i.e., height) of lower jaw (16) as compared to anvil (18). Connecting portion (624) may include an aperture (627) to allow the jaw to extend therethrough as shown in FIGS. 19A-19C. Second contact feature (626) includes an inner surface (628) and an outer surface (630), with inner surface (628) facing inner surface (620) of first contact feature (618). As shown, a cavity (632) is disposed between inner surfaces (620, 628) of first and second contact feature (618, 626). Second contact feature (626) is configured to pivot relative to first contact feature (618) between an open configuration (similar to FIG. 19A regarding applicator device (510)) and a closed configuration (shown in FIG. 20) where disposed on second contact feature (626) pushes buttress assembly (110) into contact with the stapling surface. Second contact feature (626) includes an inner portion (634) and an outer portion (not shown) but similar to outer portion (536), and a retaining portion (638). Inner portion (634) is coupled with outer portion by lateral frangible portions (not shown), but which are similar to lateral frangible portions (540, 542) described above.

FIG. 20 shows adjunct material (shown as buttress assembly (112)) being secured onto lower jaw (16) of end effector (12). As shown, applicator device (610) may load and secure buttress assembly (110) to lower jaw (16). Particularly, FIG. 20 shows a cross-sectional view of applicator device (610) and end effector (12) of FIG. 3, with arm (614) of applicator device pivoting toward lower jaw (16) that includes staple cartridge (37) of end effector (12). Outer surface (60) of lower jaw (16) is disposed 180 degrees opposite upper deck (72). As shown, buttress assembly (110) includes lower adhesive layer (120) that is configured to adhere buttress assembly (112), including buttress body (118), to upper deck (72) of staple cartridge (37) of lower jaw (16). As shown, when arm (614) is rotated toward and compressed against the end effector (12) jaw with sufficient force, the lateral frangible portions sever. This transforms inner portion (634) into a flap (not shown) with a free end that remains hingedly attached to retaining portion (638).

The application of buttress assembly (112) to lower jaw (16) that includes staple cartridge (37) may be similar to the application of buttress assembly (110) to anvil (18) described above. It may be desirable to package applicator devices (510, 610) together or applicator devices (510, 610) and buttress assemblies (110, 112) together. For example, a kit may contain one applicator device (610) and accompanying buttress assembly (110) and one applicator device (610) and accompanying buttress assembly (112). As shown, applicator devices (510, 610) are configured to apply buttress assemblies (110, 112) to the desired jaw of the end effector. Applicator devices (510, 610) may include buttress assemblies (110, 112) to be applied, and are fit individually onto each jaw, and closed, then removed to create a force limit. Applicator devices (510, 610) may close to different thicknesses to account for the different thickness of each end effector jaw. Optionally, indicia (not shown) may be disposed on applicator devices (510, 610) to indicate the desired jaw for use.

E. Fifth Exemplary Alternative Applicator Device

Figure 21:
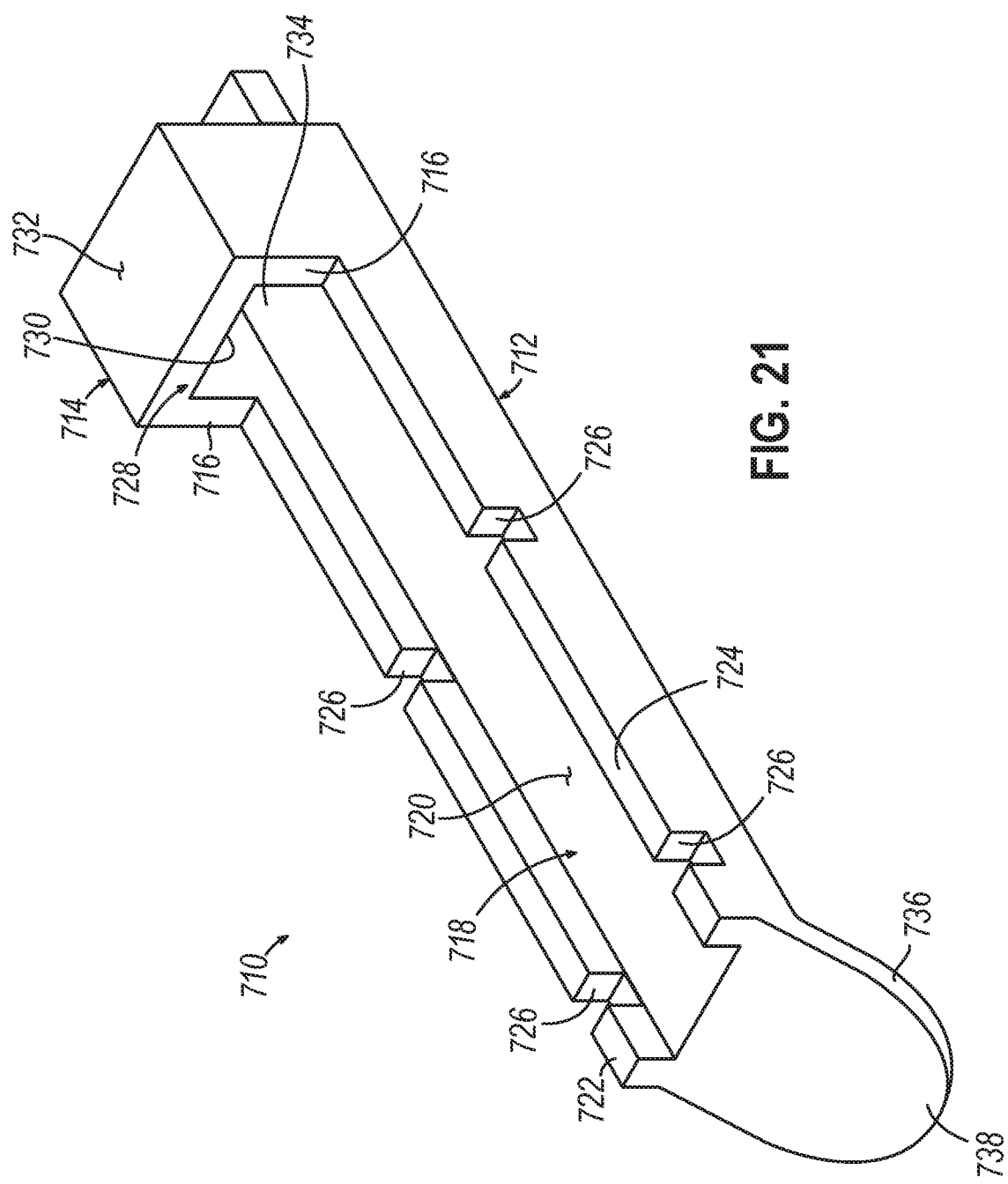
FIG. 21 depicts a perspective view of a fifth exemplary alternative applicator device.
Figure 22A:
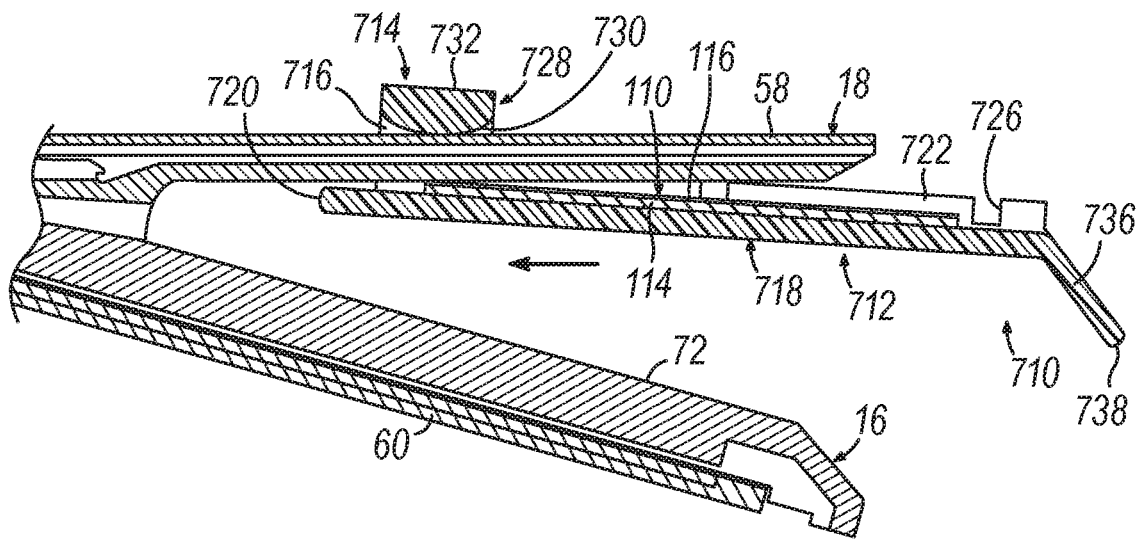
FIG. 22A depicts a cross-sectional view of the applicator device of FIG. 21, the buttress assembly of FIG. 8, and the end effector of FIG. 3, with the applicator device being moved proximally along the upper jaw of the end effector.
Figure 22B:
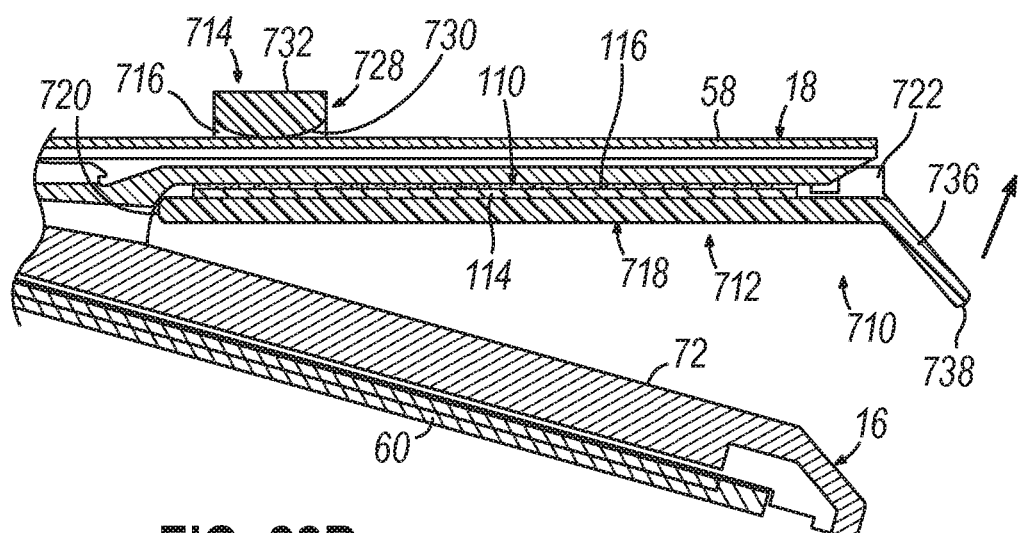
FIG. 22B depicts a cross-sectional view of the applicator device, the buttress assembly, and the end effector of FIG. 22A, with the applicator device being rotated via a tab to apply and secure the buttress assembly to the upper jaw.

FIGS. 21-22B show a fifth exemplary alternative applicator device (710) that is configured to apply an adjunct material to a jaw (e.g., anvil (18)) of end effector (12) of surgical stapler (10). As shown in FIG. 21, applicator device (710) includes a housing (712) and an arm (714). Arm (714) includes connecting portions (716) that couple with housing (712). Housing (712) includes a first contact feature (718) that is shown as a U-shaped channel. First contact feature (718) includes an inner surface (720) and opposing upward facing walls (722, 724). Upward facing walls (722, 724) include respective cutouts (726). Connecting portions (716) allow arm (714) to be used as a pivoting element to apply and secure the adjunct material (shown as buttress assembly (110)) to anvil (18). Arm (714) includes a second contact feature (728). Second contact feature (728) includes inner and outer surfaces (730, 732), with inner surface (730) facing inner surface (720) of first contact feature (718). As shown in FIGS. 21A-21B, a channel (734) is disposed between inner surfaces (720, 730) of first and second contact feature (718, 728). Housing (712) includes a downward facing tab (736) that may be used to secure buttress assembly (110) with anvil (18).

FIGS. 22A-22B show buttress assembly (110) being applied and secured onto the upper jaw (shown as anvil 18) of end effector (12). However, it is also envisioned that applicator device (710) may be modified to apply buttress assembly (112) to upper deck (72) to lower jaw (16). As shown, applicator device (710) may load and secure buttress assembly (110) to anvil (18). Particularly, FIG. 22A shows a cross-sectional view of applicator device (710) of FIG. 21 and end effector (12) of FIG. 3, with applicator device (710) being moved proximally along anvil (18). As shown in FIG. 22A, second contact feature (728) of arm (714) provides an elongate platform that a first side of the buttress assembly (110) is releasably attached to (e.g., via adhesion). Outer surface (78) of anvil (18) is disposed 180 degrees opposite contact surface (52). Second contact feature (728) is configured to be used as leverage to first contact feature (718), when second contact feature (728) pushes buttress assembly (110) into contact with the stapling surface.

FIG. 22B shows a cross-sectional view of applicator device (710) and end effector (12) of FIG. 22A, with a distal end (738) of applicator device (710) being rotated to contact anvil (18) to apply buttress assembly (110) to anvil (18). FIG. 22B shows the end effector (12) jaw being rotated downwardly so that anvil (18) is fully received within channel (734) to compressively contact buttress assembly (110) and induce adhesion using leverage provided by contact between the outer surface (58) of anvil (18) and inner surface (730) of second contact feature (728). The application of buttress assembly (112) to lower jaw (16) that includes staple cartridge (37) may be similar to the application of buttress assembly (110) described above, except that a modified version of applicator device (710) accounts for the additional thickness of lower jaw (16).

F. Sixth Exemplary Alternative Applicator Device

Figure 23:
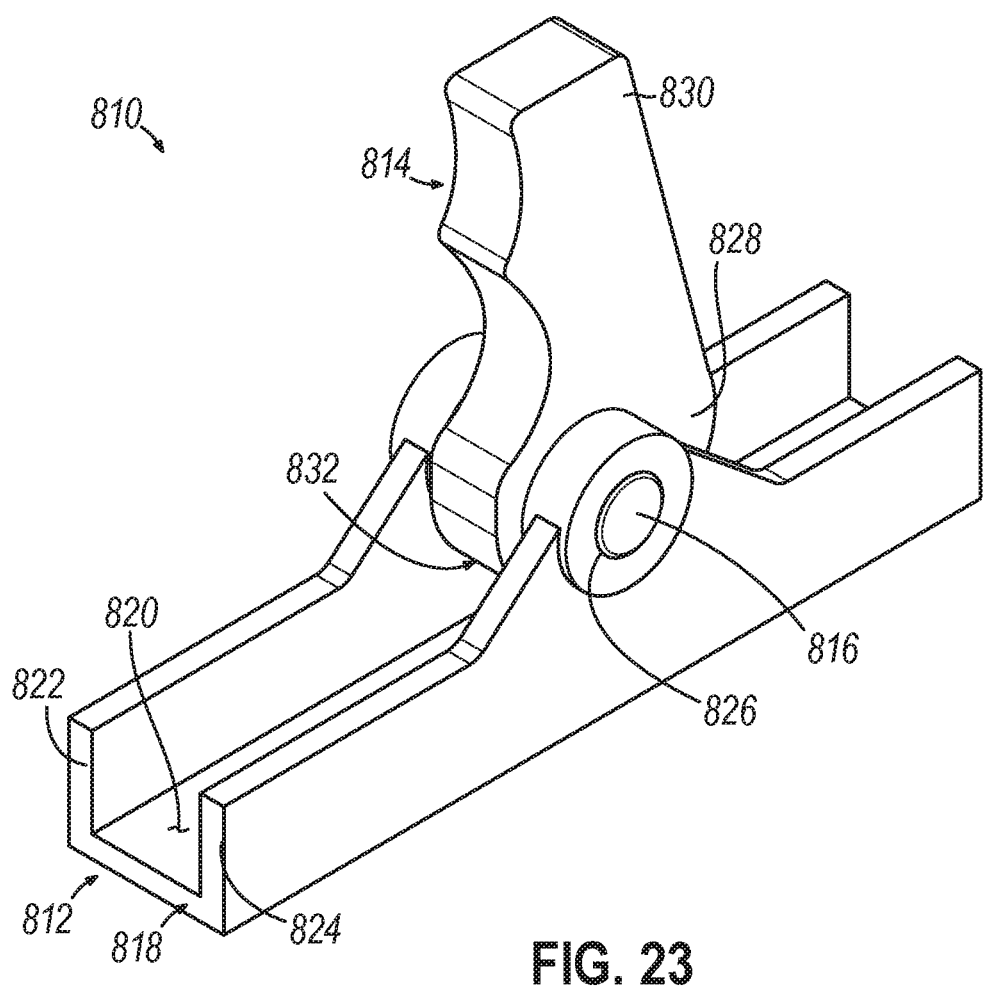
FIG. 23 depicts a perspective view of a sixth exemplary alternative applicator device.
Figure 24A:
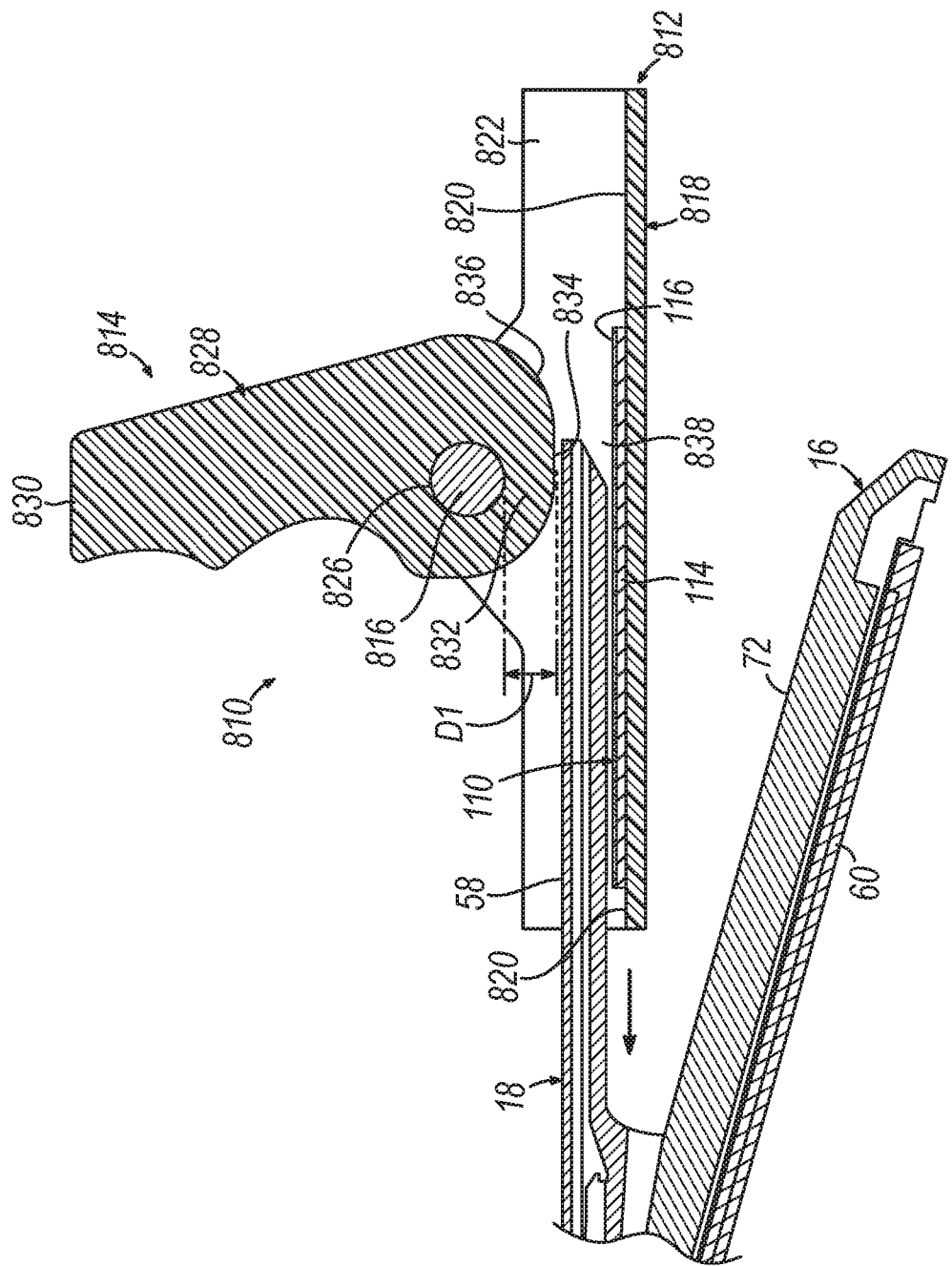
FIG. 24A depicts a cross-sectional view of the applicator device of FIG. 23, the buttress assembly of FIG. 8, and the end effector of FIG. 3, with the applicator device and the buttress assembly being moved proximally along an upper jaw of the end effector.
Figure 25:
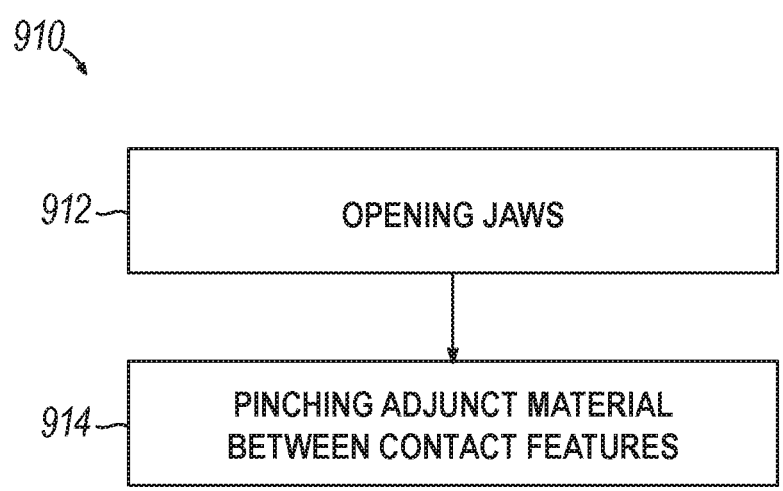
FIG. 25 depicts an exemplary method of applying a buttress assembly.

FIGS. 23-24B show a sixth exemplary alternative applicator device (810) that is configured to apply an adjunct material to a jaw (e.g., anvil (18)) of end effector (12) of surgical stapler (10). As shown in FIG. 23, applicator device (810) includes a housing (812), an arm (814), and a coupling feature (816) that pivotably couples arm (814) with housing (812). Housing (812) includes a first contact feature (818) that is shown as a U-shaped channel. First contact feature (818) includes an inner surface (820) and opposing upward facing walls (822, 824). Upward facing walls (822, 824) include apertures (826) configured to receive coupling feature (816). Coupling feature (816) allows arm (814) to pivot to apply and secure the adjunct material (shown as buttress assembly (110)) to anvil (18). Arm (814) includes a body portion (828). Body portion (828) includes a handle portion (830) disposed opposite a second contact feature (832), shown as a camming feature. Second contact feature (832) includes first and second camming surfaces (834, 836). As shown in FIG. 24A, first camming surface (834) may be separated from coupling feature (816) by a first distance (D1). A channel (838) is disposed between inner surface (820) of first contact feature (818) and first and second camming surfaces (834, 836) of second contact feature (832). As applicator device (810) is being loaded onto anvil (18), first camming surface (834) of second contact feature (832) is disposed across channel (838) from inner surface (820) of first contact feature (818)

FIGS. 24A-24B show buttress assembly (110) being secured onto the upper jaw of end effector (12). As shown, applicator device (810) may load and secure buttress assembly (110) to contact surface (52) of anvil (18). However, it is also envisioned that applicator device (810) may be modified to apply buttress assembly (112) to upper deck (72) of lower jaw (16). Particularly, FIG. 24A shows a cross-sectional view of applicator device (810) of FIG. 23 and end effector (12) of FIG. 3, with applicator device (810) being moved proximally along anvil (18). As shown in FIG. 24A, second contact feature (832) of arm (814) provides an elongate platform that a first side of the buttress assembly (110) is releasably attached to (e.g., via adhesion). Second contact feature (832) is configured to be used as leverage to first contact feature (818), when second contact feature (832) pushes buttress assembly (110) into contact with contact surface (52) of anvil (18).

FIG. 24B shows a cross-sectional view of applicator device (810) and end effector (12) of FIG. 24A, with handle portion (830) of arm (814) of applicator device (810) being rotated to contact distal portion (54) of anvil (18) to apply buttress assembly (110) to anvil (18). FIG. 24B shows the end effector (12) jaw being rotated downwardly so that anvil (18) is fully received within the channel (838) to compressively contact buttress assembly (110) and induce adhesion using leverage provided by contact between the outer surface (58) of anvil (18) and second camming surface (836) of second contact feature (832). As shown in FIG. 24B, second camming surface (836) may be separated from coupling feature (816) by a second distance (D2). The application of buttress assembly (112) to lower jaw (16) that includes staple cartridge (37) may be similar to the application of buttress assembly (110) described above, except that a modified version of applicator device (810) accounts for the additional thickness of lower jaw (16).

G. Exemplary Method of Applying Adjunct Material to End Effector Jaw

A method (910) of applying an adjunct material (e.g., buttress assemblies (110, 112) or a tissue thickness compensator) to a stapling surface (upper deck (72) or contact surface (52)) of a first jaw or a second jaw (e.g., lower jaw (16) or anvil (18)) of an end effector (12) of a surgical stapler (10) using applicator device (310, 410, 510, 610, 710, 810) is also described. At step (912), method (910) may include opening the end effector (12) jaws, such that the lower jaw (16) and anvil (18) are spaced apart. At step (914), the method (910) may include with lower jaw (16) or anvil (18) in an open configuration, pinching the adjunct material between first contact feature (324, 424, 518, 618, 718, 818) and second contact feature (330, 428, 526, 626, 728, 832) to mount the adjunct material to the stapling surface (e.g., upper deck (72) or contact surface (52)) of one of lower jaw (16) or anvil (18) of end effector (12). Buttress assemblies (110, 112) may be pinched by applying a local compression force between rollers (334, 338, 434, 444) using applicator device (310, 410) to mount adjunct material to the stapling surface of one of first or second jaws.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus configured to apply an adjunct material to a stapling surface of a jaw of a surgical stapler, wherein the jaw includes an outer surface disposed opposite the stapling surface, wherein the stapling surface includes a plurality of staple apertures or a plurality of staple forming pockets, the apparatus comprising: (a) a housing that includes a first contact feature, wherein the first contact feature is configured to contact one of the adjunct material or the outer surface of the jaw; and (b) an arm operatively coupled with the housing, wherein the arm includes a second contact feature that is configured to move relative to the first contact feature to contact the other of the adjunct material or the outer surface of the jaw, wherein the first and second contact features are configured to cooperate to apply a compression force in a direction toward the first contact feature to pinch the adjunct material against the stapling surface to mount the adjunct material to the stapling surface.

Example 2

The apparatus of Example 1, further comprising a resilient feature operatively coupled with the housing and the arm, wherein the resilient feature is configured to bias the arm, including the second contact feature, relative to the first contact feature to apply the compression force.

Example 3

The apparatus of Example 2, wherein the resilient feature includes a spring operatively coupled with the housing and the arm, wherein the spring is configured to bias the arm, including the second contact feature, relative to the first contact feature to apply the compression force.

Example 4

The apparatus of any one or more of Examples 2 through 3, wherein the resilient feature includes a tension spring, wherein the tension spring is configured to bias the arm, including the second contact feature, relative to the first contact feature to apply the compression force.

Example 5

The apparatus of any one or more of Examples 2 through 3, wherein the arm includes a platform, wherein the resilient feature includes a compression spring, wherein the compression spring in its entirety is configured to translate the platform to bias the second contact feature to apply the compression force.

Example 6

The apparatus of any one or more of Examples 1 through 5, wherein at least one of the first contact feature or the second contact feature includes a roller configured to apply the compression force and roll along the stapling surface or along the outer surface of the jaw.

Example 7

The apparatus of any one or more of Examples 1 through 5, wherein the first contact feature includes a first roller, wherein the second contact feature includes a second roller, wherein the second roller is configured to apply the compression force as the second roller rolls along the jaw.

Example 8

The apparatus of any one or more of Examples 1 through 5, wherein one of the first contact feature or the second contact feature includes first and second rollers configured to apply the compression force as the first and second rollers move along the stapling surface or the outer surface of the jaw.

Example 9

The apparatus of any one or more of Examples 1 through 5, further comprising a spool that includes a supply of the adjunct material, wherein the spool is coupled with the housing, wherein the first contact feature includes a roller that is configured to apply the adjunct material to the stapling surface.

Example 10

The apparatus of Example 9, wherein the housing further comprises a base, wherein the arm including the second contact feature that is configured to translate relative to the base to simultaneously contact the outer surface as the spool applies the adjunct material to the stapling surface.

Example 11

The apparatus of any one or more of Examples 1 through 10, further comprising a hinge that pivotably couples the arm relative to the housing at a hinge point between open and a closed configurations, wherein in the open configuration the jaw is configured to be inserted between the first and second contact features, wherein in the closed configuration the second contact feature is configured to contact the stapling surface.

Example 12

The apparatus of Example 11, wherein the second contact feature comprises: (i) inner and outer portions that are connected together by first and second lateral frangible portions, and (ii) a retaining portion disposed at an end of the second contact feature disposed opposite to the hinge, wherein the first and second lateral frangible portions are configured to break to separate the inner and outer portions but are held together by the retaining portion.

Example 13

The apparatus of any one or more of Examples 1 through 10, further comprising a hinge that pivotably couples the arm relative to housing at a hinge point, wherein the second contact feature includes first and second lateral frangible portions that are configured to sever when a predetermined pressure is applied to release the adjunct material from the apparatus.

Example 14

The apparatus of any one or more of Examples 1 through 13, wherein the adjunct material includes at least one of a buttress assembly or a tissue thickness compensator that is releasably secured with the second contact feature.

Example 15

The apparatus of any one or more of Examples 1 through 13, wherein the adjunct material includes a buttress assembly, wherein the buttress assembly includes an adhesive surface that is configured to adhere the buttress assembly to the stapling surface.

Example 16

An apparatus for loading a jaw of a surgical stapler, wherein the jaw includes a stapling surface and an outer surface disposed opposite the stapling surface, wherein the stapling surface includes a plurality of staple apertures or a plurality of staple forming pockets, comprising: (a) an adjunct material that includes a coupling feature; (b) a housing that includes a first contact feature, wherein the first contact feature is configured to contact one of the adjunct material or the outer surface of the jaw; (c) an arm operatively coupled with the housing, wherein the arm includes a second contact feature that is configured to move relative to the first contact feature to contact the other of the adjunct material or the outer surface of the jaw; and (d) a resilient feature operatively coupled with the housing and the arm, wherein the resilient feature is configured to bias the arm, including the second contact feature, relative to the first contact feature to apply a compression force in a direction toward the first contact feature to pinch the adjunct material against the stapling surface to mount the adjunct material to the stapling surface.

Example 17

The apparatus of Example 16, wherein the adjunct material includes at least one of a buttress assembly or a tissue thickness compensator.

Example 18

The apparatus of Example 16, wherein the adjunct material includes a buttress assembly, wherein the coupling feature includes an adhesive surface configured to adhere to the stapling surface.

Example 19

A method of securing an adjunct material to a stapling surface of a first jaw or a second jaw of an end effector of a surgical stapler using an apparatus, wherein the stapling surface includes a plurality of staple apertures or a plurality of staple forming pockets, wherein the apparatus includes a housing and an arm operatively coupled with the housing, wherein the housing includes a first contact feature, wherein the arm includes a second contact feature that is movable relative to the first contact feature, the method comprising: (a) separating the first and second jaws to an open configuration; and (b) with the first and second jaws in the open configuration, applying a compression force using the second contact feature to pinch the adjunct material between the first and second contact features to mount the adjunct material to the stapling surface.

Example 20

The method of Example 19, wherein the second contact feature includes a first roller, wherein the first contact feature includes a second roller, wherein applying the compression force further comprises applying the compression force to pinch the adjunct material between the first and second rollers to mount the adjunct material to the stapling surface.

Example 21

The method of any one or more of Examples 19 through 20, wherein applying the compression force further comprises applying the compression force in a direction toward the first contact feature to pinch the adjunct material against the stapling surface to mount the adjunct material to the stapling surface.

Example 22

The method of any one or more of Examples 19 through 21, wherein the apparatus includes a resilient feature operatively coupled with the housing and the arm, wherein the method further comprises biasing the arm, including the second contact feature, relative to the first contact feature to apply the compression force using the resilient feature.

Example 23

The method of Example 22, wherein the resilient feature includes a tension spring operatively coupled with the housing and the arm, wherein the method further comprises biasing the arm, including the second contact feature, relative to the first contact feature using the tension spring.

Example 24

The method of any one or more of Examples 19 through 21, wherein the arm includes a platform, wherein the resilient feature includes a compression spring, wherein the method further comprises biasing the arm, including the second contact feature, relative to the first contact feature using the compression spring to translate the platform.

Example 25

The method of any one or more of Examples 19, 21, 22, and 23, wherein at least one of the first contact feature or the second contact feature includes a roller, wherein applying the compressive force further comprises rolling the roller along the stapling surface or along the outer surface of the jaw Example 26

The method of any one or more of Examples 19, 21, 22, and 23, wherein the first contact feature includes a first roller, wherein the second contact feature includes a second roller, wherein applying the compressive force further comprises rolling the second roller along the jaw.

Example 27

The method of any one or more of Examples 19, 21, 22, and 23, wherein one of the first contact feature or the second contact feature includes first and second rollers, wherein applying the compressive force further comprises rolling the first and second rollers move along the stapling surface or the outer surface of the jaw to apply the compression force Example 28

The method of any one or more of Examples 19, 21, 22, and 23, wherein the apparatus further includes a spool that includes a supply of the adjunct material, wherein the first contact feature includes a roller, wherein applying the compressive force further comprises rolling the roller along the stapling surface to provide a compressive force while applying the adjunct material to the stapling surface.

Example 29

The method of Example 28, wherein the housing further comprises a base, wherein applying the compressive force further comprises translating the arm including the second contact feature relative to the base to simultaneously contact the outer surface as the spool applies the adjunct material to the stapling surface.

Example 30

The method of Example 19, wherein the apparatus further includes a hinge, wherein the method further comprises: (a) opening the apparatus to an open configuration where the jaw is inserted between the first and second contact features; and (b) pivoting the arm relative to the housing at a hinge point to a closed configuration where the second contact feature contacts the stapling surface.

Example 31

The method of Example 19, wherein the apparatus includes a hinge, wherein the second contact feature includes inner and outer portions that are connected together by first and second lateral frangible portions, and a retaining portion disposed at an end of the second contact feature disposed opposite to the hinge, wherein applying the compressive force further comprises rotating the arm, including inner and outer portions, towards the first contact feature to sever the first and second lateral frangible portions to separate the inner and outer portions that are still held together by the retaining portion.

Example 32

The method of Example 31, wherein severing the first and second lateral frangible portions further comprises severing the first and second lateral frangible portions when a predetermined pressure is applied to release the adjunct material from the apparatus.

Example 33

The method of any one or more of Examples 19 through 32, wherein the adjunct material includes at least one of a buttress assembly or a tissue thickness compensator, wherein applying the compression force further comprises applying the compression force using the second contact feature to pinch at least one of the buttress assembly or the tissue thickness compensator between the first and second contact features to mount at least one the buttress assembly or the tissue thickness compensator to the stapling surface.

Example 34

The method of any one or more of Examples 19 through 32, wherein the adjunct material includes a buttress assembly, wherein the buttress assembly includes an adhesive surface, wherein applying the compression force further comprises applying the compression force using the second contact feature to pinch the buttress assembly between the first and second contact features to mount the adhesive surface if the buttress assembly to the stapling surface.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/022,186, entitled "Apparatus and Method to Apply Buttress to End Effector of Surgical Stapler via Fixed Base," filed on Sep. 16, 2020, published as U.S. Pub. No. 2022/0079592 on Mar. 17, 2022; U.S. patent application Ser. No. 17/022,209, entitled "Apparatus and Method to Apply Buttress to End Effector of Surgical Stapler via Driven Member," filed on Sep. 16, 2020, published as U.S. Pub. No. 2022/0079580 on Mar. 17, 2022; U.S. patent application Ser. No. 17/022,414, entitled "Apparatus and Method to Close End Effector of Surgical Stapler onto Buttress," filed on Sep.16, 2020, published as U.S. Pub. No. 2022/0079583 on Mar. 17, 2020; U.S. patent application Ser. No. 17/022,419, entitled "Apparatus and Method to Detect Full Seating of Buttress Applicator in End Effector of Surgical Stapler," filed on Sep. 16, 2020, published as U.S. Pub. No. 2022/0079587 on Mar. 17, 2022; U.S. patent application Ser. No. 17/022,442, entitled "Apparatus and Method to Apply Buttress to End Effector of Surgical Stapler with Authentication," filed on Sep. 16, 2020, published as U.S. Pub. No. 2022/0079584 on Mar. 17, 2022; and/or U.S. patent application Ser. No. 17/022,250, entitled "Method of Applying Buttress to End Effector of Surgical Stapler," filed on Sep. 16, 2020. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus configured to apply an adjunct material to a stapling surface of a jaw of a surgical stapler, wherein the jaw includes an outer surface disposed opposite the stapling surface, wherein the stapling surface includes a plurality of staple apertures or a plurality of staple forming pockets, the apparatus comprising:
   (a) a housing that includes a first contact feature, wherein the first contact feature is configured to contact one of the adjunct material or the outer surface of the jaw; and
   (b) an arm operatively coupled with the housing, wherein the arm includes a second contact feature that is configured to move relative to the first contact feature to contact the other of the adjunct material or the outer surface of the jaw, wherein the first and second contact features are configured to cooperate to apply a compression force in a direction toward the first contact feature to pinch the adjunct material against the stapling surface to mount the adjunct material to the stapling surface.

2. The apparatus of claim 1, further comprising a resilient feature operatively coupled with the housing and the arm, wherein the resilient feature is configured to bias the arm, including the second contact feature, relative to the first contact feature to apply the compression force.

3. The apparatus of claim 2, wherein the resilient feature includes a spring operatively coupled with the housing and the arm, wherein the spring is configured to bias the arm, including the second contact feature, relative to the first contact feature to apply the compression force.

4. The apparatus of claim 2, wherein the resilient feature includes a tension spring, wherein the tension spring is configured to bias the arm, including the second contact feature, relative to the first contact feature to apply the compression force.

5. The apparatus of claim 2, wherein the arm includes a platform, wherein the resilient feature includes a compression spring, wherein the compression spring in its entirety is configured to translate the platform to bias the second contact feature to apply the compression force.

6. The apparatus of claim 1, wherein at least one of the first contact feature or the second contact feature includes a roller configured to apply the compression force and roll along the stapling surface or along the outer surface of the jaw.

7. The apparatus of claim 1, wherein the first contact feature includes a first roller, wherein the second contact feature includes a second roller, wherein the second roller is configured to apply the compression force as the second roller rolls along the jaw.

8. The apparatus of claim 1, wherein one of the first contact feature or the second contact feature includes first and second rollers configured to apply the compression force as the first and second rollers move along the stapling surface or the outer surface of the jaw.

9. The apparatus of claim 1, further comprising a spool that includes a supply of the adjunct material, wherein the spool is coupled with the housing, wherein the first contact feature includes a roller that is configured to apply the adjunct material to the stapling surface.

10. The apparatus of claim 9, wherein the housing further comprises a base, wherein the arm including the second contact feature that is configured to translate relative to the base to simultaneously contact the outer surface as the spool applies the adjunct material to the stapling surface.

11. The apparatus of claim 1, further comprising a hinge that pivotably couples the arm relative to the housing at a hinge point between open and a closed configurations, wherein in the open configuration the jaw is configured to be inserted between the first and second contact features, wherein in the closed configuration the second contact feature is configured to contact the stapling surface.

12. The apparatus of claim 11, wherein the second contact feature comprises:
   (i) inner and outer portions that are connected together by first and second lateral frangible portions, and
   (ii) a retaining portion disposed at an end of the second contact feature disposed opposite to the hinge, wherein the first and second lateral frangible portions are configured to break to separate the inner and outer portions but are held together by the retaining portion.

13. The apparatus of claim 1, further comprising a hinge that pivotably couples the arm relative to housing at a hinge point, wherein the second contact feature includes first and second lateral frangible portions that are configured to sever when a predetermined pressure is applied to release the adjunct material from the apparatus.

14. The apparatus of claim 1, wherein the adjunct material includes at least one of a buttress assembly or a tissue thickness compensator that is releasably secured with the second contact feature.

15. The apparatus of claim 1, wherein the adjunct material includes a buttress assembly, wherein the buttress assembly includes an adhesive surface that is configured to adhere the buttress assembly to the stapling surface.

16. An apparatus for loading a jaw of a surgical stapler, wherein the jaw includes a stapling surface and an outer surface disposed opposite the stapling surface, wherein the stapling surface includes a plurality of staple apertures or a plurality of staple forming pockets, comprising:
   (a) an adjunct material that includes a coupling feature;
   (b) a housing that includes a first contact feature, wherein the first contact feature is configured to contact one of the adjunct material or the outer surface of the jaw;
   (c) an arm operatively coupled with the housing, wherein the arm includes a second contact feature that is configured to move relative to the first contact feature to contact the other of the adjunct material or the outer surface of the jaw; and
   (d) a resilient feature operatively coupled with the housing and the arm, wherein the resilient feature is configured to bias the arm, including the second contact feature, relative to the first contact feature to apply a compression force in a direction toward the first contact feature to pinch the adjunct material against the stapling surface to mount the adjunct material to the stapling surface.

17. The apparatus of claim 16, wherein the adjunct material includes at least one of a buttress assembly or a tissue thickness compensator.

18. The apparatus of claim 16, wherein the adjunct material includes a buttress assembly, wherein the coupling feature includes an adhesive surface configured to adhere to the stapling surface.

19. A method of securing an adjunct material to a stapling surface of a first jaw or a second jaw of an end effector of a surgical stapler using an apparatus, wherein the stapling surface includes a plurality of staple apertures or a plurality of staple forming pockets, wherein the apparatus includes a housing and an arm operatively coupled with the housing, wherein the housing includes a first contact feature, wherein the arm includes a second contact feature that is movable relative to the first contact feature, the method comprising:
   (a) separating the first and second jaws to an open configuration; and
   (b) with the first and second jaws in the open configuration, applying a compression force using the second contact feature to pinch the adjunct material between the first and second contact features to mount the adjunct material to the stapling surface.

20. The method of claim 19, wherein the second contact feature includes a first roller, wherein the first contact feature includes a second roller, wherein applying the compression force further comprises applying the compression force to pinch the adjunct material between the first and second rollers to mount the adjunct material to the stapling surface.

* * * * *